United States Patent
Lee et al.

(10) Patent No.: US 9,714,953 B2
(45) Date of Patent: Jul. 25, 2017

(54) METHODS, DEVICES, AND REAGENTS FOR MONITORING PACLITAXEL CONCENTRATION IN PLASMA FOR PHARMACOKINETIC-GUIDED DOSING OF PACLITAXEL

(71) Applicant: Autotelic LLC, City of Industry, CA (US)

(72) Inventors: Yueh Jung Lee, Monterey Park, CA (US); Chulho Park, San Diego, CA (US)

(73) Assignee: Autotelic LLC, City of Industry, CA (US)

(*) Notice: Subject to any disclaimer, the term of this patent is extended or adjusted under 35 U.S.C. 154(b) by 0 days.

(21) Appl. No.: 14/742,513

(22) Filed: Jun. 17, 2015

(65) Prior Publication Data

US 2015/0285827 A1    Oct. 8, 2015

Related U.S. Application Data

(63) Continuation of application No. PCT/US2015/024578, filed on Apr. 6, 2015.

(60) Provisional application No. 62/051,757, filed on Sep. 17, 2014, provisional application No. 61/975,386, filed on Apr. 4, 2014.

(51) Int. Cl.
*G01N 33/94* (2006.01)
*G01N 33/558* (2006.01)

(52) U.S. Cl.
CPC ............ *G01N 33/94* (2013.01); *G01N 33/558* (2013.01); *G01N 2407/02* (2013.01); *G01N 2800/52* (2013.01)

(58) Field of Classification Search
CPC ............ G01N 33/558; G01N 2407/02; G01N 2800/52
See application file for complete search history.

(56) References Cited

U.S. PATENT DOCUMENTS

| | | |
|---|---|---|
| 5,955,621 A | 9/1999 | Durzan |
| 2010/0166746 A1 | 7/2010 | Chowdhury |
| 2012/0029172 A1 | 2/2012 | Renner |
| 2012/0034711 A1* | 2/2012 | Li ................... G01N 33/56961 436/501 |
| 2012/0064547 A1 | 3/2012 | Demuth |
| 2012/0270338 A1 | 10/2012 | Ueda |
| 2014/0010829 A1 | 1/2014 | Bigner |
| 2014/0017812 A1 | 1/2014 | Smith |

FOREIGN PATENT DOCUMENTS

WO   2012/166795 A1   12/2012

OTHER PUBLICATIONS

International Search Report and Written Opinion mailed Sep. 8, 2015, issued in corresponding Application No. PCT/US15/24578, filed Apr. 6, 2015, 21 pages.

* cited by examiner

*Primary Examiner* — Andrea S Grossman
(74) *Attorney, Agent, or Firm* — Christensen O'Connor Johnson Kindness PLLC

(57) ABSTRACT

Methods, devices, and compositions for assaying therapeutic agents. In one aspect, methods, devices, and compositions for assaying paclitaxel to provide therapeutic drug monitoring guided therapy of paclitaxel.

15 Claims, 10 Drawing Sheets

METHODS, DEVICES, AND REAGENTS FOR MONITORING PACLITAXEL CONCENTRATION IN PLASMA FOR PHARMACOKINETIC-GUIDED DOSING OF PACLITAXEL

CROSS-REFERENCE TO RELATED APPLICATIONS

This application is a continuation of International Application No. PCT/US2015/024578, filed Apr. 6, 2015, which claims the benefit of U.S. Patent Application No. 61/975,386, filed Apr. 4, 2014, and U.S. Patent Application No. 62/051,757, filed Sep. 17, 2014, each expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 53883_SEQ_Final_2015-06-17.txt. The text file is 10.4 KB; was created on Jun. 17, 2015; and is being submitted via EFS-Web with the filing of the specification.

BACKGROUND OF THE INVENTION

Paclitaxel, originally isolated from the bark of Pacific Yew tree, has been established as one of the most effective chemotherapeutic drugs for a range of cancer types including lung, ovarian, and breast cancers. A major limitation of paclitaxel is its low solubility and the need to be formulated in toxic organic solvents, typically polyoxyethylated castor oil and dehydrated ethanol mixtures (known as TAXOL®). To prevent the solvent toxicity paclitaxel has been formulated with a variety of excipients as well as using nanoparticle delivery systems that can improve the solubility of hydrophobic drugs such as paclitaxel.

ABRAXANE®, a paclitaxel albumin bound nanoparticle formulation was approved by FDA in 2005 and is currently one of the best formulations of paclitaxel for chemotherapy. Other systems have been investigated for the delivery of paclitaxel or are in development, e.g., using polymeric nanoparticles, lipid-based nanoparticle formulations, polymer conjugates, inorganic nanoparticles, carbon nanotubes, nanocrystals, or cyclodextrin nanoparticles (see, for example, Ping Ma et al., 2013, J Nanomed. Nanotechnology:4:2).

Although ABRAXANE® is a widely used chemotherapeutic agent and practically applicable to all cancer types, the response to ABRAXANE®, however, can be as low as 20%. The relative insensitivity to paclitaxel found in some patients could be a contributing factor to low response rate. However, this insensitivity may not the primary reason for the low response rate. There is up to 10-fold variations in blood concentration of paclitaxel monitored in clinical patients' samples when dosed at the various approved doses (260 mg/m$^2$ for metastatic breast cancer, 125 mg/m$^2$ for pancreatic cancer, and 100 mg/m$^2$ for lung cancer (Nyman DW et al., 2005, J Clin. Oncol. 23, 7785-93). This variation suggests that the vast majority of patients are potentially dosed incorrectly with either too great a concentration of paclitaxel administration, and had to be taken off the treatment, or too low a dosage administered and providing no benefit from the treatment. Even if patients are sensitive to paclitaxel, having an insufficient drug level would render them nonresponsive and the treatment ineffective. The under-dosed group is the most vulnerable patient population, as it is difficult to determine whether they are insensitive to paclitaxel or not administered sufficient paclitaxel. Full pharmacokinetic (PK) profiling is the only approach in such cases to provide guidance for proper drug dose based on the individual pharmacokinetic variation.

Currently there are no available methods to perform a full PK quantitation of paclitaxel without having the patient enrolled in comprehensive clinical testing, which requires a hospital stay. Typical duration of such PK testing may be over a 48 hour period and includes repetitive blood drawing. Presently, the use of complex laboratory equipment is required to analyze blood concentration of paclitaxel, including liquid chromatography/mass spectrometry (LC/MS) methods. These methods are extremely costly, currently over $120/sample and the equipment cost is in the range exceeding $150K-$200K per instrument. It has also been demonstrated that a minimum of four data points collected over a period of 48 to 72 hours is needed to adequately characterize the PK parameters for each particular patient. Keeping the patients in hospital for PK testing can easily push the cost to roughly $10,000 per patient. A sufficiently powered Phase III clinical trial to demonstrate clinical efficacy for PK guided dosing would require 500 patients (250 patients for BSA dosing and 250 patients for PK guided dosing). The bioanalytical cost alone would be $1.5M (500 points×6 cycles of chemotherapy×4 blood samplings for PK analysis×$120/sample analysis). The other components of trial would cost roughly $100,000 per patient, totaling $50M. This represents a significant barrier to obtaining meaningful clinical data necessary to guide dose adjustment for optimum tumor response and regulatory approval of the device. The high cost of the analysis and instrumentation, therefore, has prohibitive consequences on establishing therapeutic drug monitoring (TDM) for many drugs that have a relatively narrow therapeutic range.

Accordingly, a need remains for a simple, effective, and inexpensive approach to monitor the pharmacokinetics of paclitaxel in a patient, thereby appropriately personalizing the therapy to the individual patient by informing any adjustment of the dosing strategy. The present invention seeks to fulfill this need and provides further related advantages.

SUMMARY OF THE INVENTION

The present invention provides methods, devices, and compositions for assaying therapeutic agents. In one aspect, methods, devices, and compositions for assaying paclitaxel are provided.

In one aspect, the invention provides a method for assaying paclitaxel in a liquid sample. In one embodiment, the methods comprises:

(a) applying a liquid sample comprising paclitaxel to a lateral flow assay device, the device comprising (i) a sample receiving zone for receiving the liquid sample;

(ii) a detection reagent zone in liquid communication with the sample receiving zone and downstream in flow direction from the sample receiving zone, wherein the detection reagent zone comprises a detection reagent deposited thereon, wherein the detection reagent is a paclitaxel antibody, or fragment or derivative thereof that binds paclitaxel, labeled with a detectable reporting group, and wherein the paclitaxel antibody, or fragment or derivative thereof, has a $K_{on}$ from about $10^4$ to about $10^7$, and a $K_{off}$ from about $10^{-3}$ to about $10^{-7}$; and (iii) a capture zone in liquid communication with the detection reagent zone and downstream in flow direction from the detection reagent zone, wherein the capture zone comprises first and second capture reagents immobilized thereon, wherein the first capture reagent is a paclitaxel material capable of binding the detection reagent (test line), wherein the second capture reagent is an antibody capable of binding the detection reagent (control line), wherein the first capture reagent is positioned at a first distance downstream in flow direction from the upstream end of the capture zone, wherein the second capture reagent is positioned at a second distance downstream in flow direction from the upstream end of the capture zone, wherein the second distance is greater than the first distance, and wherein the ratio of the first distance to the second distance is from about 0.0 to about 0.4, when the $K_{on}$ is greater than about $2.0\times10^5$ and the $K_{off}$ is less than about $1.0\times10^{-3}$, and wherein the ratio of the first distance to the second distance is from about 0.2 to about 1.0, when the $K_{on}$ is greater than about $2.0\times10^4$ and the $K_{off}$ is less than about $2.0\times10^{-4}$; and (b) allowing the sample to flow from the sample receiving zone through the detection reagent zone to provide detection reagent with paclitaxel;

(c) allowing the detection reagent with paclitaxel to flow through the capture zone, whereby the first capture reagent (test line) competes with the analyte (paclitaxel) for binding with the detection reagent, and whereby the second capture reagent (control line) binds excess detection reagent; and (d) observing the amount of detection reagent bound to the first capture reagent (test line) relative to the second capture reagent (control line).

In certain embodiments, the method further comprising determining the quantity of paclitaxel in the sample by quantitating the amount of detection reagent bound to the first capture reagent. Quantitating the amount of detection reagent bound to the first capture reagent can include optical density measurement.

In one embodiment, the paclitaxel antibody is 3C6. In another embodiment, the paclitaxel antibody is 8A10. In certain embodiments, two paclitaxel antibodies, or fragments or derivatives thereof that bind paclitaxel are used (e.g., 3C6 and 8A10).

In the method, the paclitaxel material is a paclitaxel antigen that competes with paclitaxel for binding to the detection reagent. In one embodiment, the paclitaxel material is a paclitaxel protein conjugate.

In the methods of the invention, distance between the sample receiving zone and the first capture reagent can be varied to optimize paclitaxel detection sensitivity. In certain embodiments, the distance between the sample receiving zone and the first capture reagent is minimized to optimize paclitaxel detection sensitivity.

In certain embodiments, the method further comprises observing the amount of excess detection reagent bound to the second capture reagent (control line). In these embodiments, the method may further comprise determining the quantity of paclitaxel in the sample by quantitating the amount of detection reagent to the second capture reagent.

To enhance sensitivity and dynamic range, the method may further comprise a third capture zone intermediate the first and second capture zones, wherein the third capture zone comprises a paclitaxel material capable of binding the detection reagent. In these embodiments, determining the quantity of paclitaxel can be determined by quantitating the amount of detection reagent bound to the third capture reagent. Quantitating the amount of detection reagent bound to the third capture reagent can include optical density measurement.

It will be appreciated that the method of the invention is applicable to other solid phase assays, including, for example, surface plasmon resonance (SPR) assays.

As noted above, more than one antibody, fragment, or derivative thereof can be used in the method. In these embodiments, the first antibody can have a relatively high $K_{on}$ (e.g., greater than $1\times10^4$) and the second antibody can have a relatively low $K_{off}$ (e.g., less than $1\times10^{-3}$).

Furthermore, in certain embodiments, the capture zone can include multiple capture positions (e.g., two or three lines, T1, T2, T3) to provide multiple readings on the same sample allowing for increase reproducibility and expanded dynamic range.

In another aspect, the invention provides methods for therapeutic drug monitored (TDM) guided paclitaxel therapy. In one embodiment, the invention provides a method for monitoring the efficacy of a paclitaxel therapy in a patient diagnosed with cancer, comprising:

(a) treating a cancer patient with paclitaxel at a first point in time;

(b) determining a first concentration of paclitaxel in the patient at a first point in time, wherein determining the concentration comprises the method noted above for assaying paclitaxel;

(c) treating the patient with paclitaxel at a second point in time;

(d) determining a second concentration of paclitaxel drug in the patient at a second point in time, wherein determining the concentration comprises the method noted above for assaying paclitaxel; and (e) comparing the first and second concentrations of paclitaxel in the patient to determine the efficacy of the cancer treatment.

In a related embodiment, the invention provides a method for PK-guided dosing of paclitaxel therapy in a patient diagnosed with cancer, comprising:

(a) treating the cancer patient with paclitaxel at a first point in time;

determining one or more pharmacokinetic parameters of paclitaxel in the patient at a first point in time, wherein determining the one or more pharmacokinetic parameters comprises the method noted above for assaying paclitaxel;

(b) treating the patient with paclitaxel at a second point in time using the PK information from first dosing;

(c) determining one or more pharmacokinetic parameters of paclitaxel in the patient at a second point in time, wherein determining the one or more pharmacokinetic parameters comprises the method noted above for assaying paclitaxel; and (d) comparing one or more pharmacokinetic parameters of paclitaxel in the subject at the first point in time with the levels at the second point in time to confirm that appropriate dosing was achieved.

In certain embodiments, the pharmacokinetic parameters are selected from the group consisting of time to maximum concentration ($T_{max}$), concentration maximum ($C_{max}$), area under the curve (AUC), clearance (CL), volume of distribution ($V_d$), apparent volume of distribution during the terminal phase (Vz), apparent volume of distribution during steady state ($V_{ss}$) and combinations thereof.

In further aspects, the invention provides devices and methods, similar to those described above for paclitaxel, but that are useful for assaying other therapeutic agents.

In one embodiment, the invention provides a lateral flow device, comprising:

(a) a sample receiving zone for receiving a liquid sample;

(b) a detection reagent zone in liquid communication with the sample receiving zone and downstream in flow direction from the sample receiving zone, wherein the detection reagent zone comprises one or more detection reagents deposited thereon;

(c) a capture zone in liquid communication with the detection reagent zone and downstream in flow direction from the detection reagent zone, wherein the capture zone comprises one or more capture reagents immobilized thereon; and (d) an absorbent zone in liquid communication with the capture zone and downstream in flow direction from the capture reagent zone.

As noted above, more than one antibody, fragment, or derivative thereof can be used in the method. In these embodiments, the first antibody can have a relatively high $K_{on}$ (e.g., greater than $1 \times 10^4$) and the second antibody can have a relatively low $K_{off}$ (e.g., less than $1 \times 10^{-3}$). In one embodiment, the detection reagent comprises a first antibody having a first affinity for the therapeutic drug and a second antibody having a second affinity for the therapeutic drug, wherein the first affinity is greater than the second affinity. Furthermore, in certain embodiments, the capture zone can include multiple capture positions (e.g., two or three lines, T1, T2, T3) to provide multiple readings on the same sample allowing for increase reproducibility and expanded dynamic range.

In the method, the detection reagent is an antibody labeled with a detectable reporting group, and the capture reagent is an antigen that competes with the therapeutic drug for binding to the detection reagent or the capture reagent is an antibody capable of binding the detection reagent. In certain embodiments, the capture reagents comprise a first capture reagent that is an antigen that competes with the therapeutic drug for binding to the detection reagent, and a second capture reagent that is an antibody capable of binding the detection reagent. The first capture reagent is immobilized upstream in flow direction from the second capture reagent. The distance between the sample receiving zone and the first capture reagent can be varied to optimize detection of the therapeutic drug.

In certain embodiments, the device further includes a third capture reagent immobilized intermediate the first and second capture reagents. In this embodiment, the third capture reagent is an antigen that competes with the therapeutic drug for binding to the detection reagent.

In certain embodiments, the therapeutic agent is paclitaxel and the detection reagent comprises a monoclonal antibody selected from 8A10 and 3C6, or fragment or derivative thereof, wherein the antibody, or fragment or derivative binds to paclitaxel.

In another embodiment, the invention provides a method for assaying a therapeutic drug in a sample, comprising:

(a) applying a sample to a sample receiving zone of the device noted above; and (b) observing the amount of detection reagent bound to the one or more immobilized capture reagents.

The method can further include determining the quantity of therapeutic drug in the sample by quantitating the amount of detection reagent bound to the one or more immobilized capture reagents (e.g., detection reagent is bound to a capture reagent in a first capture position, detection reagent is bound to a capture reagent in a second capture position, detection reagent is bound to capture reagents in first and second capture positions, detection reagent is bound to capture reagents in first, second, and third capture positions).

In further embodiments, TDM guided therapy methods are provided.

In one embodiment, the invention provides a method for monitoring the efficacy of a therapeutic treatment in a patient diagnosed with a disease or condition, comprising:

(a) treating a patient with a therapeutic agent at a first point in time;

(b) determining a first concentration of the therapeutic agent in the patient at a first point in time, wherein determining the concentration comprises the methods described herein;

(c) treating the patient with the therapeutic agent at a second point in time;

(d) determining a second concentration of the therapeutic agent in the patient at a second point in time, wherein determining the concentration comprises the methods described herein; and (e) comparing the first and second concentrations in the patient to determine the efficacy of the therapeutic treatment.

In another embodiment, the invention provides a method for PK-guided dosing of a therapeutic treatment in a patient diagnosed with a disease or condition, comprising:

(a) treating the patient with a therapeutic agent at a first point in time using the PK information from first dosing;

(b) determining one or more pharmacokinetic parameters of the therapeutic agent in the patient at a first point in time, wherein determining the one or more pharmacokinetic parameters comprises assaying the therapeutic agent according to methods described herein;

(c) treating the patient with the therapeutic agent at a second point in time;

(d) determining one or more pharmacokinetic parameters of the therapeutic agent in the patient at a second point in time, wherein determining the one or more pharmacokinetic parameters comprises assaying the therapeutic agent according to the methods described herein; and (e) comparing one or more pharmacokinetic parameters of the therapeutic agent in the subject at the first point in time with the levels at the second point in time to confirm that appropriate dosing was achieved.

In certain embodiments, the pharmacokinetic parameters are one or more of time to maximum concentration ($T_{max}$), concentration maximum ($C_{max}$), area under the curve (AUC), clearance (CL), volume of distribution ($V_d$), apparent volume of distribution during the terminal phase (Vz), apparent volume of distribution during steady state ($V_{ss}$) and combinations thereof.

The above methods are applicable to disease or condition treatments that benefit from therapeutic drug monitoring. Representative diseases or conditions include cancer, inflammation, hypertension, cardiovascular, and pain. Representative therapeutic agents include paclitaxel, docetaxel, 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, and 7-L-alanylpaclitaxel.

In a further aspect, the invention provides paclitaxel antibodies. In one embodiment, the invention provides a monoclonal antibody selected from 8A10 and 3C6, or fragment or derivative thereof, wherein the antibody, antibody fragment, or antibody derivative binds to paclitaxel. In certain embodiments, the monoclonal antibody, antibody fragment, or antibody derivative comprises one or more complementary determining regions (CDRs) with at least 95% homology to a CDR contained in SEQ ID NOS: 2, 4, 6, or 8.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 5A illustrates the standard curve, i.e., the ratio of test line over control line (T/C) vs. paclitaxel concentration. The large difference in ratio for 8A10 at T1 versus T2 for the lower concentrations indicates a much higher sensitivity for this class of antibody when placed closer to the sample port, where concentration of analyte is likely to be higher.

FIG. 5B illustrates the output intensity vs. position readout of scanned test strips as provided by a reader device.

FIG. 6A illustrates the standard curve, i.e., the ratio of test line over control line (T/C) vs. paclitaxel concentration. The relatively minor difference in ratio for 3C6 at T1 versus T2 for the lower concentrations indicates a relatively low improvement in sensitivity for this class of antibody would be gained for placing the antibody closer to the sample port, where concentration of analyte is likely to be higher. This class of antibody is characterized by location independent signal from the sample port. FIG. 6B illustrates the output intensity vs. position readout of scanned test strips as provided by a reader device.

FIG. 7A illustrates the standard curve, i.e., the ratio of test line over control line (T/C) vs. paclitaxel concentration. The high sensitivity of T1 and T2 was obtained by combining the two classes of antibody (8A10 and 3C6) in the conjugate pad. This improved the dynamic range of the assay. FIG. 7B illustrates the output intensity vs. position readout of scanned test strips as provided by reader device.

DETAILED DESCRIPTION OF THE INVENTION

Today there are many therapeutic agents either in clinical use or in development. The difficulty is not in finding drugs for treatment, but in tailoring treatments to fit patients. Personalized medicine without regard to pharmacokinetic (PK) variability will result in misclassification of some patients due to either too much drug exposure resulting in toxicity among patients that would have benefitted from lower amounts of administered drug or too little drug exposure in supposedly sensitive populations. Personalized medicine with therapeutic drug monitoring (TDM) removes the PK variability and allows for correct classification of the patients according to their biomarker.

The present invention provides a point-of-care (POC) therapeutic drug monitoring (TDM) methods, devices, and related compositions for pharmacokinetic (PK)-guided dosing of therapeutic drugs.

Figure 1:
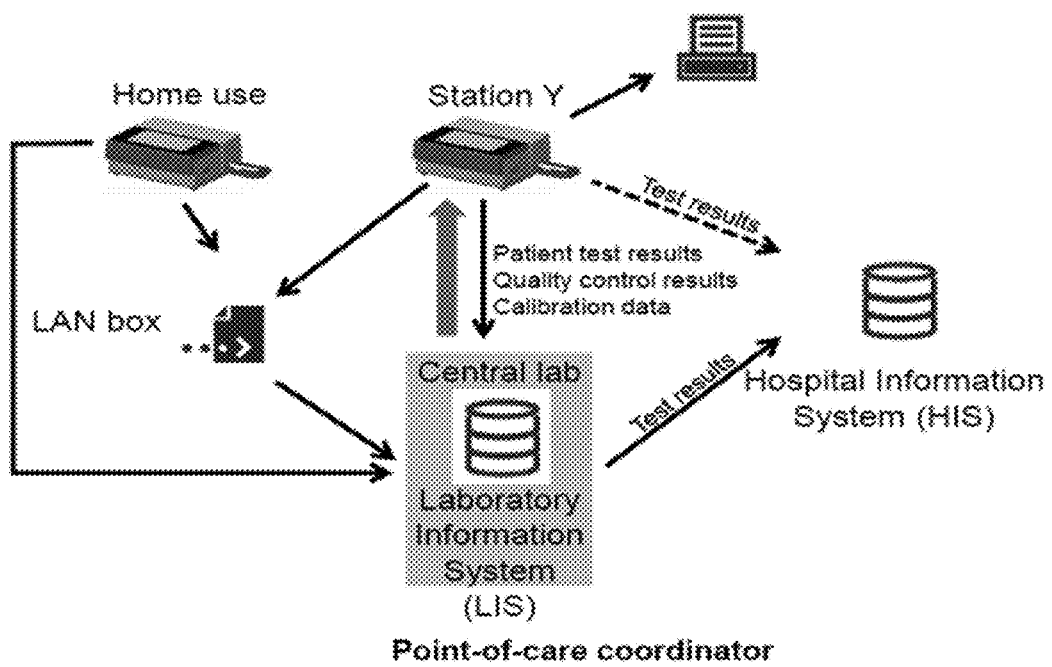
FIG. 1 is a schematic illustration of pharmacokinetic-guided dosing concept and process using a representative system and method of the invention.

FIG. 1 illustrates system characteristics, advantages and potential connectivity of the device with the hospital information system and/or laboratory information system and enabling the data transfer to the physician, ultimately supporting the drug dosage decision. The methods and devices of the invention collect the patient's therapeutic drug (e.g., paclitaxel) PK data by taking the finger-prick blood samples over a period of 24 to 48 hours and the PK data is accessed by the physician who can analyze the data and determine whether the therapeutic drug dose should be modified.

In one aspect, the invention provides methods and devices for immunoassay in general, and methods and devices for immunoassay of paclitaxel in particular. Sometimes a low level of paclitaxel in the biological sample is indicative of a need to increase dosage of paclitaxel to the subject, and a high level of paclitaxel in the biological sample is indicative of a need to decrease the dosage of paclitaxel to the subject. The methods and devices of the invention provide information useful for making adjustments to the therapeutic regime for the subject.

The assay methods and devices provided herein are described in the context of compositions, methods, and devices for the detection and monitoring of paclitaxel. However, it is appreciated that the format of the described compositions, methods, and devices are not so limited, and are readily applied more generally to monitoring any analyte of choice.

Representative Assay Methods and Devices

The present invention provides assay methods and devices for detecting or quantifying analytes (e.g., paclitaxel) in a sample.

The methods and devices can be used to assay a biological sample, such as a sample obtained from a subject (patient)

that has received a therapeutic agent (e.g., paclitaxel) for the treatment of a condition. The sample used in the assay is ultimately a liquid sample (e.g., blood, plasma, urine).

The methods of the invention are solid phase assays and therefore are suited for adaptation to other solid phase assay configurations. To exemplify the invention, the methods and devices are described using a lateral flow assay configuration. It will be appreciated that other solid phase assays know in the art can be configured in accordance with the present methods and devices.

Lateral flow assay methods and devices can be used in accordance with the present invention. Depending on the format of the lateral flow assay method and device, the assay reagents can be disposed in certain configurations. In such an embodiment, one reagent will act as a "detection reagent" and another reagent will act as a "capture reagent." Within this format, the detection reagent is generally deposited on the conjugate pad at a location between the sample port and a location where the capture reagent is deposited. The detection reagent generally comprises a detectable label, whereas the capture reagent is immobilized in its location on the pad. Thus, during operation, a liquid sample introduced in the sample port can flow along the pad. The sample will come into contact with the detection reagent first, and then subsequently flow over the capture reagent.

Figure 2A:
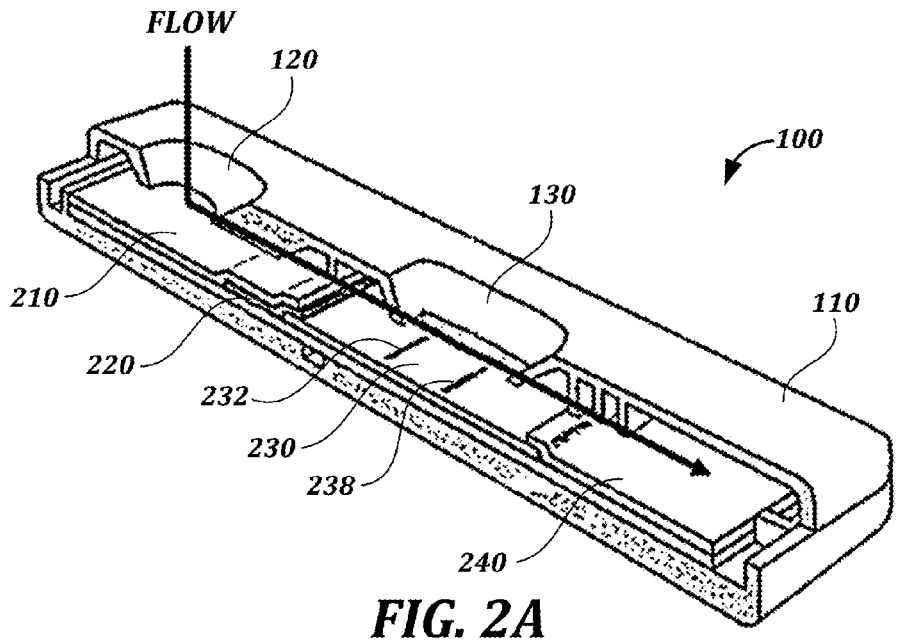
FIG. 2A is an illustration of a representative work flow for a therapeutic drug monitoring device in accordance with the invention.

A representative device for performing a lateral flow assay in accordance with the invention is illustrated in FIG. 2A. Referring to FIG. 2A, device 100 is a cassette that includes housing 110 having sample port 120, reading window 130, and test strip 200 (see FIG. 2B). In operation, a liquid sample to be analyzed is introduced to the test strip through port 120 and is flowed along the test strip as indicated by the flow direction (from sample pad 210 to absorbent pad 240. The test results can be viewed by observing the test strip through reading window 130.

Figure 2B:
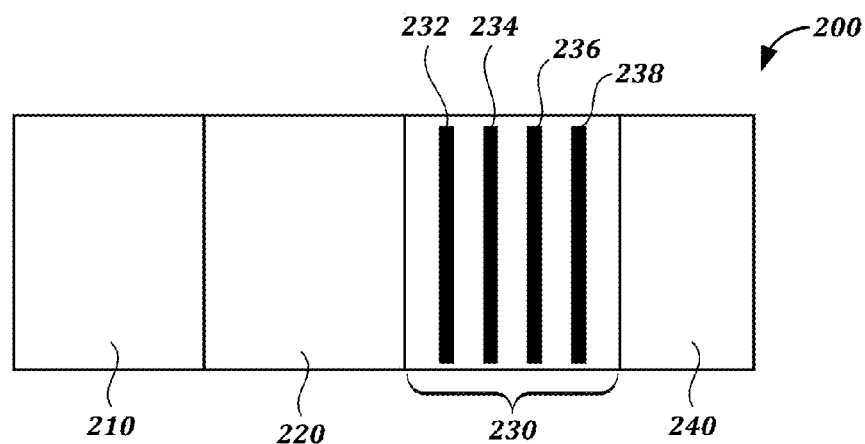
FIG. 2B is an illustration of a representative test strip for lateral flow immunoassay in accordance with the invention.

The test strip includes several zones and reagents for carrying out the assay. Referring to FIGS. 2A and 2B, representative test strip 200 includes sample pad 210, conjugate pad 220, membrane 230, and absorbent pad 240. Sample pad 210, conjugate pad 220, membrane 230, and absorbent pad 240 are in liquid communication such that liquid sample introduced to the sample pad flows through or across the conjugate pad and membrane to the absorbent pad. The size and configuration of the test strip components can be varied to suit the particular assay to be performed. For example, one or more of the component pads and membrane can overlap to facilitate optimal flow from one component to the next (sample pad 210 can overlap with conjugate pad 220, which may overlap with membrane 230, which may overlap with absorbent pad 240, as shown in FIG. 2A). The nature of the test strip zones is not particularly critical and materials for these components are known in the art.

The operation of the representative device is described as follows. Sample pad 210 receives the liquid sample to be tested. Sample flows from sample pad to conjugate pad 220.

Conjugate pad 220 includes one or more detection reagents (e.g., antibodies having an affinity for the analyte in the sample to be assayed and that are labeled to facilitate detection of the antibody in the assay).

In certain embodiments, a single detection reagent is deposited on the conjugate pad. In other embodiments, two or more detection reagents (e.g., two different antibodies, such as first and second antibodies having different affinities for the analyte to be assayed, different $K_{on}$ rates, and/or different $K_{off}$ rates) are deposited on the conjugate pad. The first and second affinities are not the same. In one embodiment, the first $K_{on}$ is greater than the second $K_{on}$. In another embodiment, the second $K_{off}$ is greater than the first $K_{off}$. The description and specification of antibody affinity, $K_{on}$, and $K_{off}$ rates described below in the context of the paclitaxel assay are applicable to the assay of therapeutic agents in general. The amount of first and second antibody deposited can be varied and need not be the same.

The detection reagent(s) deposited on conjugate pad 220 are mobilized by the liquid sample and flow with the sample to membrane 230. When analyte is present in the sample, binding between the analyte and detection reagent begins to occur once the sample contacts the detection reagents. Capture of the detection reagents, some of which may include bound analyte and some of which may not, occurs on membrane 230.

Figure 2C:
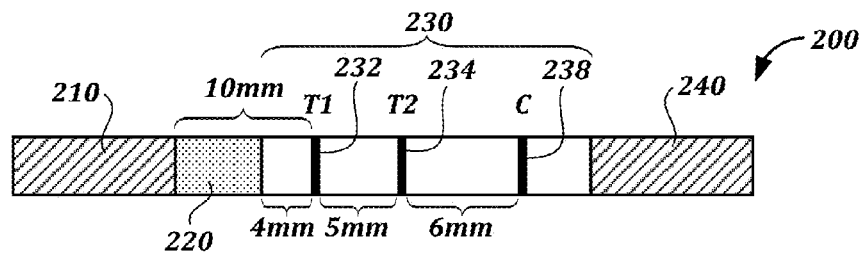
FIG. 2C is an illustration of a representative test strip for a paclitaxel lateral flow immunoassay in accordance with the invention.

Membrane 230 includes at least two capture zones: a first capture zone for capturing detection reagent that does not include bound analyte (test line) (see 232 in FIGS. 2A, 2B, and 2C) and a second capture zone for capturing excess detection reagent that does include bound analyte (control line) (see 238 in FIGS. 2A, 2B, and 2C). The first capture zone includes a first capture material (e.g., an immobilized antigen) that is effective for capturing the detection reagent that does not include bound analyte (i.e., free detection reagent). The second capture zone includes a second capture material (e.g., an immobilized antibody) that is effective for capturing the detection reagent with or without bound analyte. The amount of detection reagent captured by the first and second capture materials, respectively, will depend on the amount of analyte present in the sample. The assay described above is a competitive assay in which the analyte and first capture material compete for affinity binding to the detection reagent. The greater the amount of analyte present in the sample, the lesser the amount of detection reagent captured by the first capture material. Due to depletion of capture material, the lesser the amount of the analyte present in the sample, the more detection reagent being capture by the first capture material and therefore less available for capture by the second capture material. The ratio of the intensity of the first and second capture lines give the best value for quantitation of the analyte.

In certain embodiments, the capture zone includes two or more first capture zones (e.g., 232 and 234 in FIGS. 2B and 2C) for capturing detection reagent that does not include bound analyte. In certain embodiments, the capture zone includes two or more second capture zones (e.g., 236 and 238 in FIG. 2B) for capturing detection reagent.

The illustrated approach of the lateral flow cassette can utilize any compatible reader with the appropriate sensitivity for detection of signal from the flow cassette and the ability to calibrate and quantify such a signal. Beneficial features of any reader can include ease of use features, including touch screen, integrated RFID or integrated barcode reader, and the capacity to easily export results, such as to a memory card or USB stick. The reader preferably has pre-installed software facilitating an interface in a selection of languages. The reader preferably has a high memory capacity to facilitate storage of multiple (such as >1000) results and can save >100 distinct test method protocols. The reader can contain connectivity to facilitate its integration into a larger system, such as through LAN or WLAN connectivity to LIS or cloud based data storage and management systems. Finally, multiple USB ports are desirable for additional connectivity capacities, such as to facilitate connection to external printers, and the like.

A representative reader is the Qiagen's Reader ESEQuant LFR (commercially available from Qiagen, Germany), which has been demonstrated as a compatible effective reader for the inclusion of the lateral flow cassette described herein. This reader is a small, portable device with internal rechargeable battery allowing it to operate out in the field and serves the requirements of the point-of-care (POC) device. The lateral flow cassette is scanned using a confocal camera system embedded in the reader. On board image analysis system is fully functional with the bar code reader of the lateral flow cassettes so that analysis method can be easily uploaded to the device.

Detection Reagents. In certain embodiments, the detection reagent is at least one antibody, antibody fragment, or antibody derivative, as described herein. The detection reagent is capable of binding the analyte in the sample (e.g., paclitaxel) and when the detection reagent does not bind paclitaxel in the sample, the detection reagent binds to the capture reagent.

The detection reagents include a moiety or label that can provide a detectable signal capable of reliable quantification. Suitable moieties include those known in the immunoassay art that provide colorimetric, fluorescent, chemiluminescent, enzymatic, or radiometric signals. Representative moieties include that those provide a detectable signal that is visual and may not require instrumentation to read (e.g., colored moieties or enzymes that generate colored moieties or enzymatic. Quantitation is typically achieved through instrumental analysis of the detectable signal. In one embodiment, the detection reagent is an antibody labeled with colloidal gold, which can be visually observed.

Gold colloids are generated from reduction of gold chloride with a monodisperse nature, which are of a controlled and uniform diameter, such as 40 nm monodisperse colloid. An antibody is conjugated with colloidal gold through passive absorption.

As noted above, in preferred embodiments, multiple (i.e., more than one type of) antibodies, antibody fragments, or antibody derivatives are used. In some embodiments, the multiple (distinct) antibodies, antibody fragments, or antibody derivatives are combined and deposited in the same location on the test strip (i.e., conjugate pad).

Two distinct anti-paclitaxel antibodies are described herein, 3C6 and 8A10. The 3C6 antibody is highly specific for paclitaxel, whereas the 8A10 antibody is less specific for paclitaxel and has a broader affinity to taxanes in general. Although, the two antibodies behave similarly in traditional competitive ELISA, it was surprisingly found that in solid phase lateral flow assays, the signal provided by 8A10 was improved by moving the first capture reagent (e.g., T1 location) closer to the sample port, as compared to 3C6, which was independent of location (T1 or T2). T1 being close to the sample application is exposed to higher concentration of the analyte, and T2 being further from the sample application is exposed to lower concentration of the analyte. This is a surprising finding that optimal placement of the capture line(s) is related to the Kon and Koff values of the antibodies used in the method. The availability of 3C6 allows for construction of multiple line devices wherein the high Kon antibody (e.g., 8A10) is deposited as close to the sample origin as possible and the low Koff antibody (e.g., 3C6) is deposited along the pad to provide a second/third/fourth, etc., readout.

Accordingly, various modifications can be made to the lateral flow cassette device to facilitate or confer various detection properties. For example, to expand the dynamic range of the device, multiple test lines (T1, T2, etc.) with the use of multiple affinity antibodies, the dynamic range and/or the reproducibility of the assay can be expanded. The description and specification of positioning capture reagents (T/C) on the test strip described below in the context of the representative paclitaxel assay is applicable to positioning of capture reagents in assay of the invention in general.

The preparation of representative detection reagents (e.g., paclitaxel antibody-colloidal gold conjugate) useful in the assays of the invention are described in Example 1.

Capture Reagents. The capture reagents serve to capture the detection reagent allowing for observation and quantitation of a detectable signal in the assay. As noted above, the assay methods and devices include first and second capture materials immobilized at first and second capture zones, respectively.

In one embodiment, the capture reagent is an immobilized analyte (e.g., paclitaxel complex), which is an immobilized antigen when the detection reagent is an antibody, that captures detection reagent that does not include bound analyte. The immobilized analyte can be directly immobilized to the test strip. Alternatively, the immobilized analyte can be immobilized via a linker or carrier material (e.g., analyte conjugated to a carrier protein, such as albumin). In such an embodiment, the capture reagent is the first capture material as described above.

In one embodiment, the capture reagent is an immobilized antibody that captures detection reagent that captures detection reagent with or without bound analyte. In embodiments in which the detection reagent is a mouse monoclonal antibody, the capture reagent is an anti-mouse antibody (e.g., goat anti-mouse antibody, GAM antibody). In such an embodiment, the capture reagent is the second capture material as described above.

The preparation of representative capture reagents (e.g., BSA-paclitaxel) useful in the assays of the invention are described in Example 1.

Alternative Assay Configurations. The lateral flow assay of the invention described herein is a solid phase immunoassay. It will be appreciated that the format of the assay and device can be inverted from the format described above such that the detection reagent is the labeled antigen (e.g., BSA-paclitaxel with detectable label) and the capture reagent is the one or more antibody, antibody fragment, or antibody derivative (i.e., immobilized in the capture zone). In the operation of such a format, the sample flows through/across the deposited labeled antigen and subsequently contacts the immobilized antibody, antibody fragment, or antibody derivative. At that point, the free analyte (e.g., paclitaxel) initially present in the sample competes with the labeled antigen for binding to the immobilized antibody, antibody fragment, or antibody derivative. As above, the device can include multiple, distinct antibodies, antibody fragments, or antibody derivatives immobilized at the same or different locations. The capture reagent can be at the same or different locations. In all embodiments where the test strip has multiple locations where capture reagent is immobilized, an appropriate reader is used that can detect signal in those locations.

It is noted that the present devices, systems, compositions, and methods are generally described herein in terms of a lateral flow assay. However, the general strategy for monitoring an antigen of choice, as described herein, does not need to be limited to lateral flow assay formats, but can applied to other assay formats, such as other solid phase immunoassays (surface plasmon resonance assays), which are generally well-known in the art. Accordingly, notwithstanding description addressing lateral flow format, the present disclosure also encompasses devices, systems, compositions, and methods that incorporate any known assay format. In some embodiments, the assay format includes immobilization of capture reagents, such as the antigen conjugate (e.g., paclitaxel conjugate) or antigen binding reagents (e.g., anti-paclitaxel antibodies, fragments, derivatives) on a substrate. The substrate can be any known appropriate substrate for an assay format, such as nitrocellulose or glass. In some embodiments, the substrate is a nanostructure. In some embodiments, the substrate can comprise or consist of carbon nanostructures, such as carbon nanotubes, to which the capture reagents can be immobilized.

Representative Paclitaxel Assay. FIG. 2C is an illustration of a representative test strip for a paclitaxel lateral flow immunoassay in accordance with the invention.

Referring to FIG. 2C, representative test strip 200 includes sample pad 210, conjugate pad 220, membrane 230 with first capture zones 232 and 234 (T1 and T2) and second capture zone 238 (C), and absorbent pad 240. As noted above with regard to FIGS. 2A and 2B, sample pad 210, conjugate pad 220, membrane 230, and absorbent pad 240 are in liquid communication such that liquid sample introduced to the sample pad flows through or across the conjugate pad and membrane to the absorbent pad; the size and configuration of the test strip components can be varied to suit the paclitaxel assay to be performed (e.g., one or more of the component pads and membrane can overlap to facilitate optimal flow from one component to the next, as shown in FIG. 2A).

In one embodiment, the invention provides a method for assaying paclitaxel in a liquid sample, comprising (a) applying a liquid sample comprising paclitaxel to a lateral flow assay device, the device having (i) a sample receiving zone for receiving the liquid sample;

(ii) a detection reagent zone in liquid communication with the sample receiving zone and downstream in flow direction from the sample receiving zone, wherein the detection reagent zone comprises a detection reagent deposited thereon, wherein the detection reagent is a paclitaxel antibody, or fragment or derivative thereof that binds paclitaxel, labeled with a detectable reporting group; and (iii) a capture zone in liquid communication with the detection reagent zone and downstream in flow direction from the detection reagent zone, wherein the capture zone comprises first and second capture reagents immobilized thereon, the first capture reagent positioned upstream in flow direction from the second capture reagent, wherein the first capture reagent is a paclitaxel material capable of binding the detection reagent, and wherein the second capture reagent is an antibody capable of binding the detection reagent;

(b) allowing the sample to flow from the sample receiving zone through the detection reagent zone to provide a detection reagent with paclitaxel (e.g., combination of detection agent with bound paclitaxel, optionally free detection reagent, and optionally free paclitaxel);

(c) allowing the detection reagent with paclitaxel to flow through the capture zone, whereby the first capture reagent binds free detection reagent to provide detection reagent bound to the first capture reagent, and whereby the second capture reagent binds detection reagent with or without bound paclitaxel; and (d) observing the amount of detection reagent bound to the first capture reagent relative to the second capture reagent.

In certain embodiments, the method further comprises determining the quantity of paclitaxel in the sample by quantitating the amount of detection reagent bound to the first capture reagent. Quantitating the amount of detection reagent bound to the first capture reagent includes optical density measurements, among others.

Suitable detectable reporting groups are described above. In one embodiment, the detectable reporting group is colloidal gold.

The paclitaxel antibody, or fragment or derivative thereof, useful in the present methods have a $K_{on}$ greater than about $1 \times 10^4$. Representative $K_{on}$ values are greater than about $2 \times 10^4$, $4 \times 10^4$, $8 \times 10^4$, $1 \times 10^5$, $1 \times 10^6$, and $1 \times 10^7$). Preferred ranges are from about $1 \times 10^4$ to about $1 \times 10^7$.

The paclitaxel antibody, or fragment or derivative thereof, useful in the present methods have a $K_{off}$ less than about $1 \times 10^{-3}$. Representative $K_{off}$ values are less than about less than about $1 \times 10^{-3}$, $1 \times 10^{-4}$, $1 \times 10^{-5}$, and $1 \times 10^{-7}$. Preferred $K_{off}$ values range from about $1 \times 10^{-3}$ to $1 \times 10^{-7}$.

In certain embodiments, the paclitaxel antibody, or fragment or derivative thereof, has a $K_{on}$ from about $1 \times 10^4$ to about $1 \times 10^6$ and a $K_{off}$ from about $1 \times 10^{-3}$ to about $1 \times 10^{-4}$.

Methods for determining the $K_{on}$ values and $K_{off}$ values are described in Example 4.

In one embodiment, the antibody has a high $K_{on}$ and low $K_{off}$ (e.g., minimum $K_{on}$ is $2.0 \times 10^5$ and maximum $K_{off}$ is $1.0 \times 10^{-3}$). In this embodiment, the capture line is placed at 0.0 to 0.4 T/C. For this class, monoclonal antibody engineering would focus on keeping $K_{off}$ constant while increasing $K_{on}$ as much as possible. The greater the $K_{on}$ the better is the antibody detection.

In another embodiment, the antibody has a low $K_{on}$ and high $K_{off}$ (e.g., minimum $K_{on}$ is $2.0 \times 10^4$ and maximum $K_{off}$ is $2.0 \times 10^{-4}$. In this embodiment, the capture line is placed at 0.2-1.0 T/C. For this class, monoclonal antibody engineering would focus on keeping $K_{on}$ constant while decreasing $K_{off}$ as much as possible. The lower the off rate the better is the antibody for detection.

In certain embodiments, the paclitaxel antibody is 3C6. In other embodiments, the paclitaxel antibody is 8A10. In further embodiments, combinations of paclitaxel antibodies can be used (e.g., 3C6 and 8A10). These antibodies are described in detail below.

In the assay, the first capture zone includes an immobilized paclitaxel material that serves is a paclitaxel antigen that competes with paclitaxel for binding to the detection reagent. The first capture zone captures detection reagent that does not include bound paclitaxel (i.e., free detection reagent). In certain embodiments, the paclitaxel material is a paclitaxel protein conjugate. Suitable protein conjugates include serum albumin conjugates, such as BSA-paclitaxel.

In the assay, the second capture zone includes an immobilized antibody capable of binding the detection reagent. In certain embodiments, the antibody is a goat anti-mouse antibody.

As noted above, the paclitaxel detection sensitivity in the assay can be optimized by varying the distance between the point at which the sample is introduced to the lateral flow device (e.g., sample receiving zone) and the first capture reagent. In certain embodiments, the distance between the sample receiving zone and the first capture reagent is minimized to optimize paclitaxel detection sensitivity. In certain embodiments, the distance is less than 20 mm, less than 10 mm, less than 5 mm, less than 3 mm, less than 2 mm, or less than 1 mm. In certain embodiments, the distance is from 20 to 1 mm, 10 to 1 mm, 5 to 1 mm, 3 to 1 mm, or 2 to 1 mm.

The optimization can be described as relative positioning of T (test line) and C (control line): T/C, which is defined as the distance from origin to T/distance from origin to C ratio, where the origin is defined as the upstream edge of the capture zone (upstream edge of membrane 230 in FIGS. 2A-2C). T/C can be greater than about 0.0 (i.e., first capture reagent is located at upstream edge of capture zone), or about 0.01, about 0.02, about 0.04, about 0.08, about 0.10, about 0.20, about 0.40, about 0.80, or less than about 1.0 (i.e., first capture reagent is located at the downstream edge of the capture zone, with second capture reagent located intermediate the first capture reagent and the downstream edge of the capture zone). Preferably, T/C is from about 0.2 to about 0.7.

In certain embodiments, the ratio of the first distance to the second distance is from about 0.0 to about 0.40. In other embodiments, the ratio of the first distance to the second distance is from about 0.20 to about 1.0.

In certain embodiments, the amount of excess detection reagent that is bound to the second capture reagent is observed and measured. In certain embodiments, determining the quantity of paclitaxel in the sample is determined by relating the final capture reagent (test line) to the second capture reagent (control line).

As noted above, representative assay of the invention include more than one first capture reagents in more than one first capture zone. In certain of these embodiments, the method further includes a third capture zone (see T2, 234 in FIG. 2C) intermediate the first (T1, 232 in FIG. 2C) and second (C, 238 in FIG. 2C) capture zones, wherein the third capture zone comprises a paclitaxel material capable of binding the detection reagent. The paclitaxel material in the first and third zones can be the same or different. In certain of these embodiments, the quantity of paclitaxel in the sample is determined by quantitating the amount of detection reagent bound to the first and second capture reagents. Quantitating the amount of detection reagent bound to the first and second capture reagents can include optical density measurement.

In certain embodiments of the method, the lateral flow device further comprises an absorbent zone in liquid communication with the capture reagent zone and downstream in flow direction from the capture reagent zone.

Figure 3:
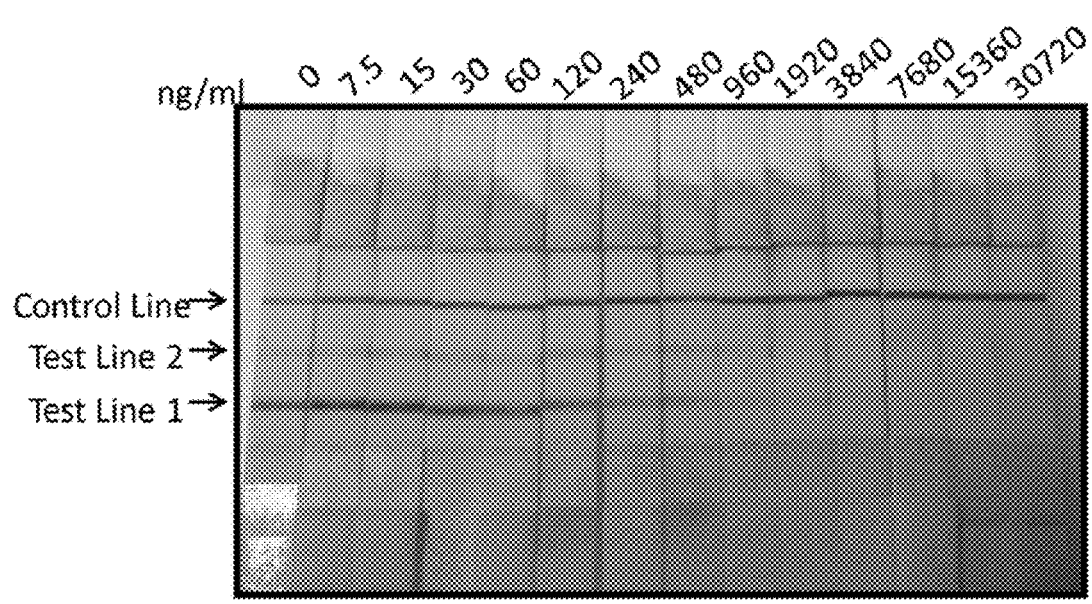
FIG. 3 is an image of representative test strips subject to assay conditions in accordance with the present invention in which the amount of a representative analyte (paclitaxel) was varied. In this assay configuration, the test strip includes three capture zones: Test Line 1 and Test Line 2 show capture using immobilized antigen (paclitaxel, in the form of immobilized BSA-paclitaxel) as the first capture material; Control Line shows capture using an immobilized antibody (goat anti-mouse antibody, GAM) as the second capture material. In this assay the detection reagent was an anti-paclitaxel antibody (8A10) labeled with colloidal gold.

FIG. 3 is an image of representative test strips subject to assay conditions in which the amount of a representative analyte (paclitaxel) was varied. In these assay configurations, membrane 230 includes three capture zones: Test Line 1 and Test Line 2 show capture using immobilized antigen (paclitaxel, in the form of immobilized BSA-paclitaxel) as the first capture material; Control Line shows capture using an immobilized antibody (goat anti-mouse antibody) as the second capture material. In this assay the detection reagent was an anti-paclitaxel antibody (8A10) labeled with colloidal gold.

It is noted that the methods and devices of the invention are useful for detecting levels of paclitaxel, including any formulation of paclitaxel or paclitaxel prodrug, in a biological sample. The formulations of paclitaxel include any known agents to facilitate delivery of paclitaxel, such as polymeric nanoparticles, lipid-based nanoparticle formulations, polymer conjugates, inorganic nanoparticles, carbon nanotubes, nanocrystals, and cyclodextrin nanoparticles.

The description of a representative lateral flow immunoassay in accordance with the methods and devices of the invention is described in Example 3.

Paclitaxel Antibodies

In another aspect, the invention provides antibodies (e.g., monoclonal antibodies or mAbs) that bind paclitaxel. The mAbs, referred to as 8A10 and 3C6, were purified from an antibody-rich harvested medium using MabSelect (GE Healthcare, Pittsburgh, Pa.). The mAbs were selected based on their binding to BSA-paclitaxel, which was prepared as described in J-G Leu et al., Cancer Res. (1993) 53:1388-1391.

In one aspect, the invention provides a monoclonal antibody selected from 8A10, 3C6, and fragments or derivatives thereof, wherein the antibody, antibody fragment, or antibody derivative binds paclitaxel.

As used herein, the term "antibody" encompasses antibodies and antibody fragments thereof, derived from any antibody-producing mammal (e.g., mouse, rat, rabbit, camelid, and primate, including human) or synthetically or recombinantly produced, that specifically binds to a target of interest (e.g., paclitaxel) or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof, such as an antigen binding fragment. As described herein, monoclonal antibodies are preferable because they provide for increased specificity in binding of the antigen of choice, such as a therapeutic drug (e.g., paclitaxel).

As used herein, the term "antigen binding fragment" refers to the antigen binding or variable region from or related to a full-length antibody. Illustrative examples of antibody fragments include Fab, Fab', F(ab)$_2$, F(ab')$_2$, and Fv fragments, scFv fragments, diabodies, nanobodies, linear antibodies, single-chain antibody molecules, and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "derivative" indicates that the antibody or antibody fragment has been produced from a reference antibody. For example, sometimes it is desirable to modify or enhance binding characteristics of a reference antibody. Thus, the antibody can be subjected to various modifications, including mutations subjected to the encoding DNA, to alter binding properties. The resulting antibody with altered properties is then referred to as a "derivative" of the reference antibody. For example, an antibody derivative can be an antibody that contains mutations resulting from affinity maturation processes that were applied to the reference antibody (or the nucleic acids encoding the reference antibody). Such mutations can result in antibodies with altered (e.g., improved) binding affinity, selectivity, and the like.

In some embodiments, the antibody, antibody fragment, or antibody derivative comprises one or more complementary determining regions (CDRs) with at least 95% homology to a CDR contained in SEQ ID NOS: 2, 4, 6, or 8. SEQ ID NOS: 2 and 4, described in more detail below, are the amino acid sequences of the variable region of the 8A10 light and heavy chains, respectively. SEQ ID NOS: 6 and 8, also described in more detail below, are the amino acid sequences of the variable region of the 3C6 light and heavy chains, respectively. Each variable region contains three complementary determining regions (CDRs), which are indicated below. In some embodiments, the antibody, antibody fragment, or antibody derivative comprises one, two, or all three of complementary determining regions (CDRs) with at least 95% homology to one, two, or all three of the CDRs contained in any one SEQ ID NOS: 2, 4, 6, or 8. In some embodiments, the antibody, antibody fragment, or antibody derivative has a heavy and light chain, which comprise one, two, three, four, five, or all six, of the CDR regions provided by the 8A10 variable light and heavy regions (in SEQ ID NOS: 2 and 4). In some embodiments, the antibody, antibody fragment, or antibody derivative has a heavy and light chain, which comprise one, two, three, four, five, or all six, of the CDR regions provided by the 3C6 variable light and heavy regions (in SEQ ID NOS:6 and 8).

In some embodiments, the one or more CDRs have a sequence identity with at least 95%, 96%, 97%, 98%, 99%, or 100% homology to one or more CDRs in any one SEQ ID NOS: 2, 4, 6, or 8. As used herein, the term "percent homology" or "percent homologous," when used in connection with a polypeptide used in the practice of the present invention, is defined as the percentage of amino acid residues in a polypeptide sequence that are homologous with the amino acid sequence of a specified polypeptide after aligning the sequences to achieve the maximum percent homology. When making the comparison, no gaps are introduced into the biomarker sequences in order to achieve the best alignment. Amino acid sequence homology can be determined, for example, in the following manner. The amino acid sequence of a polypeptide is used to search a protein sequence database, such as the GenBank database using the BLASTP program.

The program is used in the ungapped mode. Default filtering is used to remove sequence homologies due to regions of low complexity. The default parameters of BLASTP are utilized.

The production, processing, purification, characterization, and optimization of representative paclitaxel antibodies (3C6 and 8A10) useful in the assay methods of the invention are described in Example 2. The antibodies of the invention were generated by immunizing mice with either TAXOL® or baccatin conjugated to KLH. The antibodies are summarized as: 3C6 anti- TAXOL® IgG$_{2a,k}$, 3H5 anti-baccatin III IgG$_1$, 8A10 anti-taxane IgG$_{2a}$. Cross-reactivity profile of 3C6, 3H5, and 8A10 antibodies are shown by their IC$_{50}$ values towards various taxanes in Table 1.

TABLE 1

| Paclitaxel Antibody Cross-Reactivity. | | | |
| --- | --- | --- | --- |
| Taxane | 3C6 | 3H5 | 8A10 |
| paclitaxel (TAXOL ®) | 10 nM | >316 nM | 7 nM |
| 10-deacetyltaxol | 15 nM | >333 nM | 10 nM |
| 7-epi-10-deacetyltaxol | 25 nM | >333 nM | 15 nM |

TABLE 1-continued

| Paclitaxel Antibody Cross-Reactivity. | | | |
| --- | --- | --- | --- |
| Taxane | 3C6 | 3H5 | 8A10 |
| 7-xylosyl-10-deacetyltaxol | 30 nM | >286 nM | 17 nM |
| 7-epi-taxol | 80 nM | >316 nM | 50 nM |
| cephalomannine | 220 nM | >325 nM | 8 nM |
| baccatin III | >511 nM | 10 nM | 12 nM |
| baccatin V | >460 nM | 10 nM | 10 nM |
| 10-deacetylbaccatin III | >551 nM | 230 nM | 21 nM |
| 7-epi-10-deacetylbaccatin III | >469 nM | 150 nM | 27 nM |
| TAXOTERE ® (docetaxel formulation) | >318 nM | >318 nM | 10 nM |
| 2-debenzoyl-2-(p-trifluoromethylbenzoyl)taxol | >293 nM | >293 nM | >293 nM |
| 20-acetoxy-4-deacetyl-5-epi-20,O-secotaxol | >310 nM | >310 nM | >293 nM |

In order to effectively utilize antibodies in diagnostic applications to achieve a dynamic detection range, the two key factors that need to be successfully optimized are the antibodies' specificity and affinity toward the targeted antigen. The 3C6 and 8A10 monoclonal antibodies have high specificity and affinity to paclitaxel, which indicates that these specifically bind to a single epitope of the targeted paclitaxel antigen in a highly homogeneous manner. This specificity also helps eliminate cross reactivity problems in a detection assay. In conjunction with specificity, monoclonal antibodies can also have optimized and improved affinities toward the antigen in order to achieve a dynamic detection range in diagnostic tests, which can be achieved by the process of affinity maturation. Additionally, the mAb can be selected for rapid K$_{on}$ to be compatible with the rapid flow assay.

Figure 4:
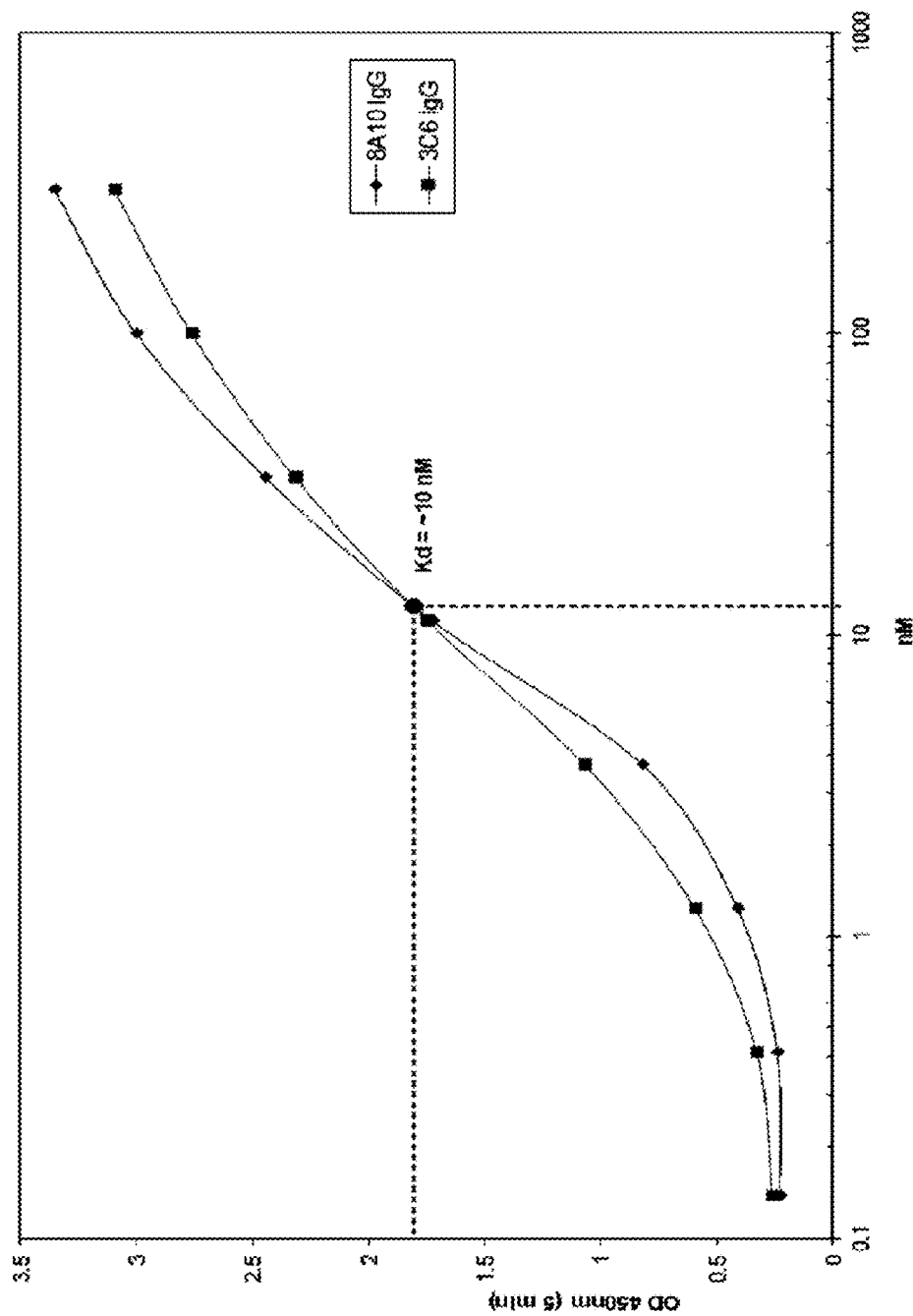
FIG. 4 is a graph illustrating direct binding of intact IgGs (8A10 and 3C6) of the invention to a BSA-paclitaxel antigen on an ELISA.

As illustrated in FIG. 4, both the 3C6 and 8A10 monoclonal antibodies have apparent K$_d$ values of about 10 nM with a sensitivity limit of about 100-200 ng/mL.

The following examples are provided for the purpose of illustrating, not limiting, the invention.

EXAMPLE 1

Assay Reagents

In this example, the preparation of representative detection reagents and capture reagents useful in the assay methods and devices of the invention are described.

Detection reagents: antibody-colloidal gold conjugates. Briefly, antibodies (see Example 2) were diluted to 1 mg/mL in 0.5×PBS and the following steps were taken: (1) shake or swirl gold to resuspend any settled gold then place 0.5 mL Naked Gold sol into 10 clean individual test tubes; (2) each tube was labeled with the pH value (or 1 through 10) from the provided pH charts; (3) pH charts were used to add varying amounts of buffer in microliters to each test tube, and shake to mix; (4) place each tube on a low speed vortexer and add the antibody solution, and mix thoroughly (about 2 to 3 seconds), for the 20 nm gold, 14 µL of a 2 mg/mL solution of antibody or protein is optimal; (5) a deepening purple color and/or black precipitate on some tubes indicate that the antibody or protein is below its isoelectric point, leading to cross-linking of individual gold solutions (cross-linked solutions cannot be used in immunological assays are discarded; deep purple solutions are mostly inactive as well; only tubes with a slight purple color or no change in color are useful for immunological assays; (6) allow the reaction to continue for a total of 30 minutes; and (7) stop the reaction by the addition of 50 µL of blocking solution.

Capture reagents: paclitaxel-albumin conjugates. Paclitaxel-albumin conjugates (e.g., BSA-paclitaxel) were prepared as described in J-G Leu et al., Cancer Res. (1993) 53:1388-1391 was generally followed. For synthesis of 2'-hemisuccinitaxol, the crystals are the starting material for conjugation of the taxol to carrier protein. Taxol (20 mg) and succinic anhydride (36 mg) were dried for 4 h at room temperature under vacuum over $P_2O_5$ and dissolved in 480 µL of dry pyridine. After standing at room temperature overnight, the pyridine was removed under vacuum and the residue was washed once with 2 mL of distilled water. Acetone (1 mL) was added, and distilled water was added dropwise to the acetone solution until a few crystals (2'-hemisuccinyltaxol) appeared. The mixture was kept at 4° C. for 3 h and the crystals were recovered by filtration and dried under vacuum. The product yield was 70%.

The dialysis step removes any unconjugated taxol. 2'-Hemisuccinyltaxol (10 mg) was dissolved in 1 mL DMSO and 300 µL acetonitrile, and 50 µL (35 mg; 0.19 mmol) of n-tributylamine was then added. The mixture was cooled to 4° C. in an ice bath, and 25 µL (25 mg; 0.18 mmol) of isobutylchloroformate was added to the mixture which was kept on ice for 30 min. The solution was added dropwise into a BSA solution [25 mg, $(3.73 \times 10^{-4}$ mmol) in 3 mL of distilled water, pH 9.5, at 4° C.]. The pH was adjusted immediately to 7.5 with 1N HCl and the mixture was kept at 4° C. overnight and dialyzed against PBS at 4° C. overnight.

In one exemplary embodiment, a lateral flow system was evaluated. A 0.5 mg/mL BSA-paclitaxel (Test line) and 0.5 mg/mL goat anti-mouse antibody (Control line) were striped onto the system's membrane. Paclitaxel antibody-colloidal gold conjugate was flowed through the system. The antibody-colloidal gold conjugate bound to BSA-paclitaxel immobilized on the membrane and generated a strong signal. The signal was specific to paclitaxel because a decreased signal was observed when paclitaxel was added to the spiked into the samples.

EXAMPLE 2

Paclitaxel Antibodies

In this example, the production, processing, purification, characterization, and optimization of representative paclitaxel antibodies useful in the methods and devices of the invention are described.

Antibody production and processing. Cells were grown in CCM1 (Hyclone) with 5-10% FBS and 1×Pen/Strep. Cells were split (1:4) once they reached densities of $>1 \times 10^6$ cells/mL. Cells were then frozen and stored in 2 separate liquid nitrogen cryogenic tanks as backups. Cells were cultured in roller bottles until a density of $1 \times 10^6$ cells/mL was reached. At that point, cultures were no longer fed and cell viability was monitored daily. Once cell viability decreased to <50%, cells were removed and the antibody-rich medium was harvested.

Affinity purification of antibody. Diafiltration was performed using PBS, pH 7.4 and the harvested antibody was concentrated 10-fold using a 50 Kd cut-off membrane. MabSelect (GE Healthcare, Pittsburgh, Pa.) was used for affinity purification. The hydrophilic, high-flow agarose bead, optimized for both capacity and throughput, and the oriented coupling of the rProtein A ligand, deliver a product pool that is high in purity and yield.

Purification run program.
Column: XK 16/40 (16 mm i.d., 20 cm bed height).
Sample: Clarified hybridoma spent media.

Loading Buffer A: 20 mM $NaH_2PO_4$, 0.15 M NaCl, pH 7.2.

Elution Buffer B: 0.1 M Na3-citrate, pH 3.6.

Antibody affinity. A plot of the results of direct binding of intact IgGs (8A10 and 3C6) to BSA-paclitaxel antigen is shown in FIG. 4. 50 µL of BSA-paclitaxel antigen at a concentration of 3.5 µg/mL in 1×PBS was bound to a plate and incubated at 4° C. overnight. The plate was washed four ties with PBS/0.05% Tween 20. The plate was blocked for 2 hours with 1% BSA in PBS/0.05% Tween 20 at room temperature. The plate was washed four ties with PBS/0.05% Tween 20. 50 µL of antibody sample (8A10 and 3C6) was bound (start at 300 nM and titer down by 3 s). The plate was washed four times with PBS/0.05% Tween 20. 50 µL of goat anti mIgG horseradish peroxidase (1:5000 dilution) was bound and then 50 µL of substrate solution TMB was added and the color allowed to develop. The reaction was stopped with 50 µL 1M HCl and the optical density was read at 450 nm. The results of direct binding of intact IgGs (8A10 and 3C6) to BSA-paclitaxel antigen are shown in FIG. 4.

Antibody optimization. Antibody optimization was performed that included affinity maturation. This approach involves: (1) characterizing the antibodies by sequencing antibodies produced from hybridoma cell lines, (2) constructing antibody libraries focused on CDR regions; (3) screening for beneficial mutations, and (4) combining beneficial mutations.

Step 1: Cloning and Expression of Anti-Paclitaxel mAb as a Fab

A. Sequencing of Variable Regions of Antibodies (8A10 and 3C6) Produced from Hybridoma Cells.

i. Total RNA extraction and mRNA denaturation

Total RNA was extracted from the two hybridoma cells (8A10 and 3C6) using QIAGEN RNeasy Mini Kit. The mRNA mix (described below) was incubated at 72° C. for 3 min, then cooled down to 42° C. for 2 min. After cooling, the tube was spun briefly for 10 seconds at 14,000×g to collect the content at the bottom.

| mRNA Mix | |
| --- | --- |
| RNA template (0.2-0.4 ug) | 1-2.75 uL |
| 5'-RAGE primer A | 1 uL |
| RNase-free water | to 3.75 uL | ii. cDNA Synthesis and 5' RAGE Reaction cDNA synthesis and 5' RAGE reaction were performed as shown below.

| cDNA synthesis | | 5' RAGE reaction | |
| --- | --- | --- | --- |
| SMARTer II A oligo | 1 uL | 2X PCR mix | 10 uL |
| 5X First-strand buffer | 2 uL | cDNA | 1 uL |
| DTT (20 mM) | 1 uL | 10X Universal Primer mix | 2 uL |
| dNTP mix (10 mM) | 1 uL | Reverse primer | 1 uL |
| RNase inhibitor | 0.25 uL | RNase-free water | 6 uL |
| SMARTScribe RT | 1 uL | | |
| mRNA mix after dent | 3.75 uL | | |
| Total | 10 uL | | 20 uL | iii. Analysis of PCR Reaction by Agarose Gel Electrophoresis

Products of PCR amplification were electrophoresed on an agarose gel to confirm the presence of amplicons corresponding the light and heavy chain variable regions of the 8A10 and 3C6 mAbs.

iv. Cloning, Sequencing and CDR Analysis

The PCR positive bands were cloned into a vector and sequenced. Antibody sequence analysis identified one light chain and one heavy chain for 8A10 and 3C6. Initially for 3C6, only one light chain and no heavy chain (aberrant sequence) were identified. Therefore, a specific primer, designed according to the sequence obtained from the N-terminal sequencing results, was utilized to re-PCR the heavy chain. Consequently, identification of a heavy chain for 3C6 was accomplished.

8A10 Hybridoma

The 8A10 hybridoma sequencing results are set forth below.

The 8A10 Variable Light Chain nucleic acid sequence is SEQ ID NO: 1:

```
                                           (SEQ ID NO: 1)
GAC ATT GTG ATG ACC CAG TCT CAA AAA TTC ATG TCC

ATA ACA CTA GGA GAG AGG GTC AGC ATC ACC TGC AAG

CCC AGT CAG AAT GTG GGT TCT GCT GTA ACC TGG TGG

CAA CAG AAA CCA GGA CAA TCT CCT AAA CTA CTG ATT

TAC TCA GCT TCC AAT CGG TAT ACT GGA GTC CCT GAT

CGC TTC ACA GGC AGT GGA TCT GGG ACA GAT TTC ACT

CTC ACC ATT AGT AAT GTG CAG TCT GAA GAC CTG GCA

GAT TAT TTC TGT CAA CAA TAT AGC AGC TAT CCG TAC

ACG TTC GGA GGG GGG ACC AAG CTG GAA ATA AAA CG.
```

The sequences encoding the CDR regions are underlined.

The corresponding 8A10 Variable Light Chain amino acid sequence is SEQ ID NO: 2:

```
                                           (SEQ ID NO: 2)
DIVMTQSQKFMSITLGERVSITCKPSQNVGSAVTWWQQKPGQSPKLLIYS

ASNRYTGVPDRFTGSGSGTDFTLTISNVQSEDLADYFCQQYSSYPYTFGG

TKLEIKR.
```

The three CDR regions are underlined (i.e., CDRL1 is KPSQNVGSAVT (SEQ ID NO: 9), CDRL2 is SASNRYT (SEQ ID NO: 10), CDRL3 is QQYSSYPYT (SEQ ID NO: 11)).

The 8A10 Variable Heavy Chain nucleic acid sequence is SEQ ID NO: 3:

```
                                           (SEQ ID NO: 3)
GAG GTC CAG CTG CAA CAA TCT GGA CCT GAA CTG GTG

AAG CCT GGG GCT TCA GTG AAG ATT TCC TGT AAG GCT

TCT GGA TAC ACG TTC ACT GAC TCC ACC ATG AAC TGG

GTG AAG CAG AGC CAT GGA AAG AGC CTT GAG TGG ATT

GGA GAG ATT GAT CCT AAC AAT GGT GGT ACT AAC TAC

AAT CAG AAG TTC AAG GGC AAG GCC ACA TTG ACT GTA

GAC AAG TCC TCC AGC ACA GCC TAT ATG GAG CTC CGC

AGC CTG ACA TCT GAG GAC TCT GCA GTC TAT TAC TGT

GCA AGA GGG GTC TGG GGC CAA GGC ACC ACT CTC ACA

GTC TCC TCA.
```

The sequences encoding the CDR regions are underlined.

The corresponding 8A10 Variable Heavy Chain amino acid sequence is SEQ ID NO: 4:

```
                                           (SEQ ID NO: 4)
EVQLQQSGPELVKPGASVKISCKASGYTFTDSTMNWVKQSHGKSLEWIGE

IDPNNGGTNYNQKFKGKATLTVDKSSSTAYMELRSLTSEDSAVYYCARGV

WGQGTTLTVSS.
```

The three CDR regions are underlined (i.e., CDRH1 is GYTFTDSTMN (SEQ ID NO: 12), CDRH2 is EIDPNNGGTNYNQKFKG (SEQ ID NO: 13), and CDRH3 is GV).

3C6 Hybridoma

The 3C6 hybridoma sequencing results are set forth below.

The 3C6 Variable Light Chain nucleic acid sequence is SEQ ID NO: 5:

```
                                           (SEQ ID NO: 5)
GAT GTT GTG ATG ACC CAA ACT CCA CTC TCC CTG CCT

GTC AGT CTG GGA GAT CAA GCC TCC ATC TCT TGC AGA

TCT CGT CAG AGC CTT GTA CAC AGT AAT GGA AAC ACC

TAT TTA CAT TGG TAC CTG CAG AAG CCA GGC CAG TCT

CCA AAG CTC CTG ATC TAC AAA GTT TCC AAC CGA TTT

TCT GGG GTC CCA GAC AGG TTC AGT GGT AGT GGA TCA

GGG ACA GAA TTC ACA CTC GAG ATC AGC AGA GTG GAG

GCT GAG GAT CTG GGA GTT TAT TTC TGC TCT CAA AGT

ACA CAT GTT CCT CCG ACG TTC GGT GGA GGC ACC AAG

CTG GAA ATC AAA C.
```

The sequences encoding the CDR regions are underlined.

The corresponding 3C6 Variable Light Chain amino acid sequence is SEQ ID NO: 6:

```
                                           (SEQ ID NO: 6)
DVVMTQTPLSLPVSLGDQASISCRSRQSLVHSNGNTYLHWYLQKPGQSPK

LLIYKVSNRFSGVPDRFSGSGSGTEFTLEISRVEAEDLGVYFCSQSTHVP

PTFGGGTKLEIK.
```

The three CDR regions are underlined (i.e., CDRL1 is RSRQSLVHSNGNTYLH (SEQ ID NO: 14), CDRL2 is KVSNRFS (SEQ ID NO: 15), and CDRL3 is SQSTHVPPT (SEQ ID NO: 16)).

The 3C6 Variable Heavy Chain nucleic acid sequence is SEQ ID NO: 7:

```
                                           (SEQ ID NO: 7)
GAG GTG CAG CTT CAG GAG TCG GGA CCT AGT CTC GTG

AAA CCT TCT CAG ACT CTG TCC CTC ACC TGT TCT GTC

ACT GGC GAC TCC ATC ACC AGT GGT TAC TGG AAC TGG

ATC CGG AAA TTC CCA GGG AAT AGA CTT GAG TAC ATG

GGG TAC ATA AGC TAC AGT GGT AGC ACT TAC TAC AAT

CCG TCT CTC AAA AGT CGA ATC TCC ATC ACT CGA GAC

ACA TCC AAG AAC CAG TAC TAC CTA CAT TTG ACT TCT
```

-continued

```
GTG ACT ACT GAG GAC ACA GCC ACA TAT TAC TGT GCC

CAA GGG GAT GGC GCC TAC TGG GGC CAA GGC ACC ACT

CTC ACA GTC TCC TCA.
```

The sequences encoding the CDR regions are underlined.

The corresponding 3C6 Variable Heavy Chain amino acid sequence is SEQ ID NO: 8:

(SEQ ID NO: 8)
EVQLQESGPSLVKPSQTLSLTCSVT<u>GDSITSGYWN</u>WIRKPGNRLEYMGY<u>I

SYSGSTYYNPSLKS</u>RISITRDTSKNQYYLHLTSVTTEDTATYYCAQ<u>GDGA

YW</u>GQGTTLTVSS.

The three CDR regions are underlined (i.e., CDRH1 is GDSITSGYWN (SEQ ID NO: 17), CDRH2 is YISYS-GSTYYNPSLKS (SEQ ID NO: 18), and CDRH3 is GDGAY (SEQ ID NO: 19)).

lacZ promoter. The double-stranded DNA coding for the VL, C kappa, and VH regions of 8A10 and 3C6 mAbs were ligated into the phage-based vector containing the gene for the constant region of the CH1 region of a human IgG1. The DNA was transformed into *E. coli* and the resulting plaques containing phage was examined in detail. Plaques were picked at random, their DNA isolated and the sequence determined. Clone 8A10_1 was determined to have the identical sequence for the VL, C kappa, and VH regions as that of mAb 8A10 (not shown). The cloning process for 3C6 can be performed according to the same protocol.

C. Demonstration of Paclitaxel Binding Activities of the Fabs Generated from the M13 Engineering Vector.

A Clone 8A10_1 phage-infected culture of XL1-Blue *E. coli* (gram-negative) was grown while being induced with IPTG, was harvested via centrifugation and the periplasmic contents were released by osmotic shock (periprep). The released Fab products were isolated from the culture. The Fab concentration was quantified by ELISA and antigen specific binding of the Fab was done using paclitaxel ELISA

TABLE 2

Comparison of N-terminal sequencing results with hybridoma sequencing results for 8A10 and 3C6 mAbs.

| | 8A10 | | | | 3C6 | | |
|---|---|---|---|---|---|---|---|
| | | Hybridoma sequencing data | | | | Hybridoma sequencing data | |
| Residue | N-terminal sequencing data Calls | Variable Light Chain | Variable Heavy Chain | Residue | N-terminal sequencing data Calls | Variable Light Chain | Variable Heavy Chain |
| 1 | D, Q, F, (S, H, M) | D | | 1 | D, E | D | E |
| 2 | H, I, L, (V) | I | | 2 | V | V | V |
| 3 | V, S, Q, (T, K) | V | | 3 | Q, (V) | V | Q |
| 4 | M, E, N, F | M | E | 4 | M, L | M | L |
| 5 | T, Q, V, (.R) | T | Q | 5 | Q, T | T | Q |
| 6 | Q, Q, N, Y | Q | L | 6 | Q, E | Q | E |
| 7 | S, L, F, E | S | Q | 7 | T, S | T | S |
| 8 | Q, Q, Y, D | Q | Q | 8 | G, P | P | G |
| 9 | K, F, N, Q | K | S | 9 | L, P | L | P |
| 10 | S, D, F, L | F | G | 10 | S | S | S |
| 11 | M, N, L, G | M | P | 11 | L | L | L |
| 12 | S, P, L | S | E | 12 | V, P | P | V |
| 13 | I, T, E, L, (V) | I | L# | 13 | K, V | V | K |
| 14 | (T, G) | T | V | 14 | S, P | S | P |
| 15 | V, K, L | L | K | 15 | S, L | L | S |
| 16 | K, P, G | G | P | 16 | Q, G | G | Q |
| 17 | E, P | E | G | 17 | D, T | D | T |
| 18 | R, (H, G) | R | A | 18 | Q, L | Q | L |
| 19 | V, A, (L) | V | S | 19 | A, S | A | S |
| 20 | S, S, H, (R, L) | S | V# | 20 | L, S | S | L |
| 21 | I | I | K | 21 | T, I | I | T |
| 22 | K, T, R | T | I | 22 | S, (R) | S | C# |
| 23 | I | C* | S | 23 | (S) | C# | S |
| 24 | S, K | K | C* | 24 | R, V | R | V |
| 25 | P | P | K | 25 | T | S# | T |
| 26 | K, (A), (S) | S | A | 26 | G, (R) | R | G |
| 27 | Q, (A) | Q | S# | 27 | D, Q | Q | D |
| 28 | N | N | G | 28 | (S) | S | S |
| 29 | V, (G) | V | Y | 29 | I, (L) | L | I |
| 30 | (Y), (T), (G) | G | | 30 | (T, V) | V | T |

*Cysteine sequence cannot be determined by N-terminal sequencing
Residues of discrepancy between n-terminal seq. results and hybridoma seq. results.

B. Cloning of Variable Regions of mAb into M13 Engineering Vector.

The DNA coding for the VL, C kappa, and VH regions of the mAbs (i.e., 8A10 and 3C6) were amplified with sequence specific primers using PCR. The resulting PCR product was gel-purified and restriction digested for specific sites within the M13-based phage vector under the control of together with intact IgGs (not shown). The $K_d$ values (approximately 10 nM for both antibodies) of the two intact IgGs were comparable to the ones previously reported (see FIG. 3). The $K_d$ value of Fab 8A10 was determined to be 10 nM as well, which is the same as that of intact IgG 8A10. These results suggest that the correct variable region sequence of the parental antibody 8A10 exists in the present Fab 8A10 and is correctly folded and expressed in the Fab format from the M13 engineering vector.

The Fab expressed sufficiently well in the periplasmic prep to demonstrate concentration-dependent binding to BSA-paclitaxel conjugate coated wells.

EXAMPLE 3

Representative Solid Phase Competitive Assay

In this example, a representative assay demonstrating the efficacy of a solid-phase competitive assay is described. The assay demonstrates the utility of using the anti-paclitaxel antibodies described herein in such a detection format to provide informative signals for the present of paclitaxel in a sample. The results demonstrate that variable placement of the antibodies can enhance assay performance.

Paclitaxel lateral flow system. 1.2 mg/mL BSA-Pac (test lines, T) and 0.2 mg/ml of goat-anti-mouse antibody (control line, C) were striped onto a membrane card (high-flow plus HF180 membrane card, Millipore). Anti-paclitaxel antibody-colloidal gold conjugate was absorbed into and the dried onto a conjugate pad (glass fiber pad, Millipore). Fetal bovine serum (FBS) spiked with paclitaxel (10 uL), chased by 80 μL of PBS Tween, was flowed in the assay.

Tandem Antibody Assay. The antibody-gold conjugates are reconstituted using distilled water and are then added to each other to make the appropriate concentrations. This tandem antibody solution is applied and then dried onto the assay conjugate pads.

Reader Output: Intensity vs Position. Readout of the results of scanning the test strips. The strips were read using Qiagen reader (Qiagen, Germany).

Paclitaxel Standard Curve. Standard curves of ratio of test line over control line vs. paclitaxel concentration were generated.

Figure 5A:
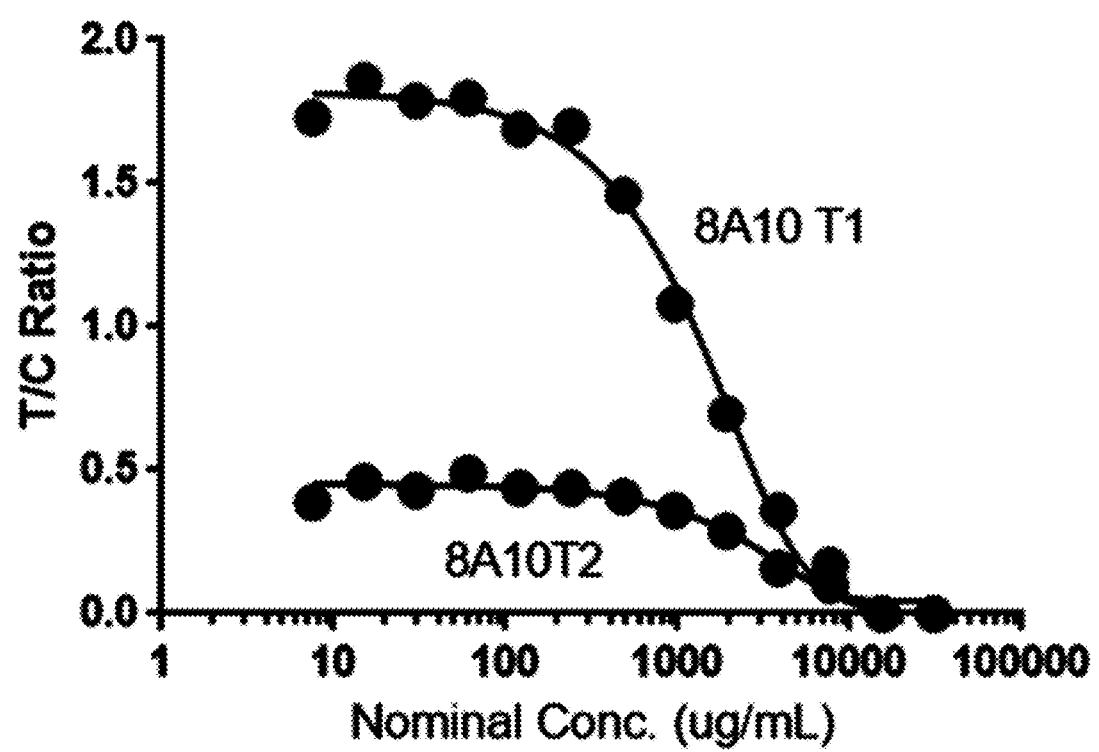
FIGS. 5A and 5B illustrate curves for 8A10 bound at lines T1 and T2 in a representative lateral flow assay of the invention carried out using a device as schematically illustrated in FIG. 2C and as described in Example 3.
Figure 5B:
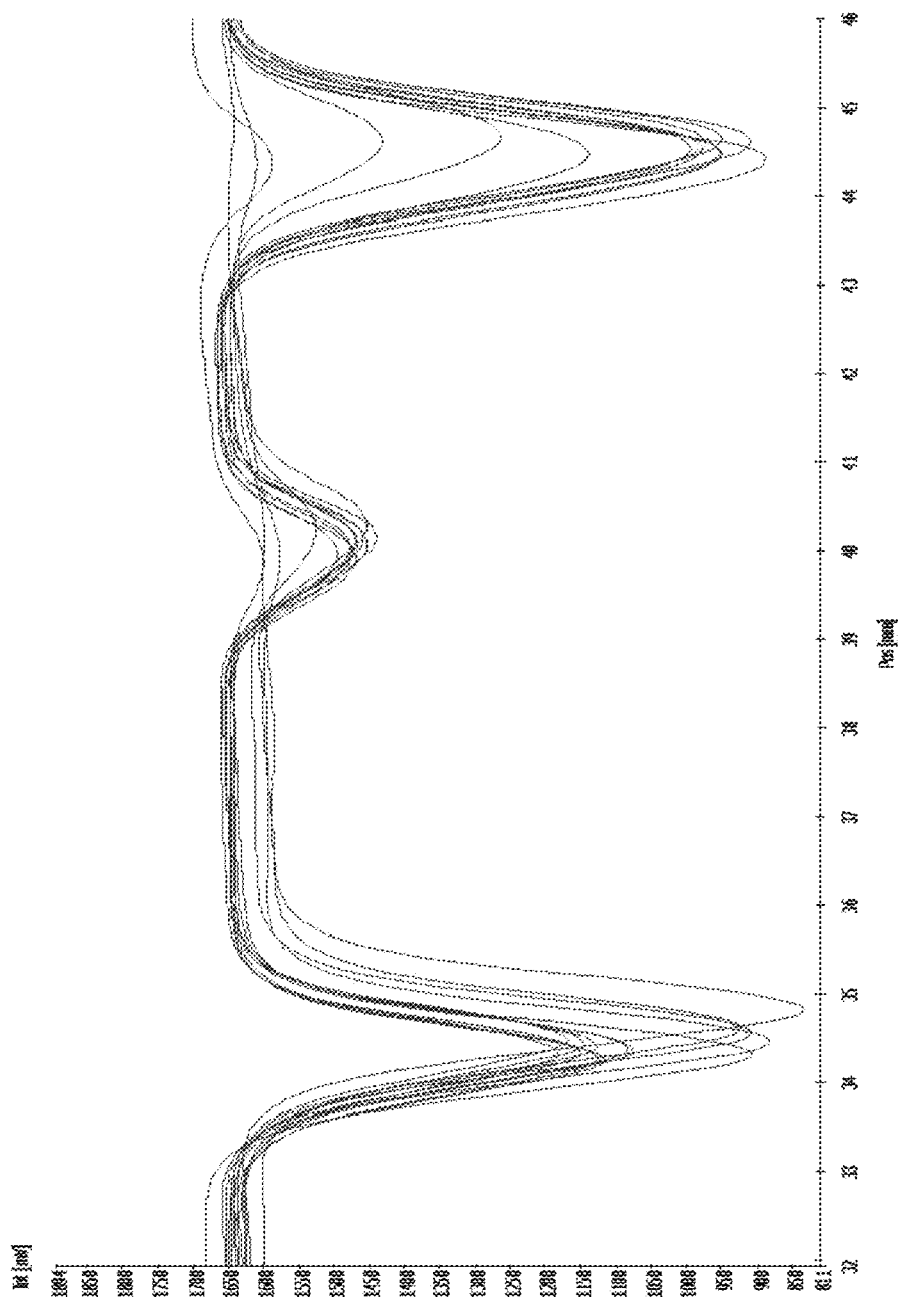

FIGS. 5A and 5B illustrate curves for 8A10 bound at lines T1 and T2. FIG. 5A illustrates the standard curve, i.e., the ratio of test line over control line (T/C) vs. paclitaxel concentration. The large difference in ratio for 8A10 at T1 versus T2 for the lower concentrations indicates a much higher sensitivity for the antibody when placed closer to the sample port, where concentration of analyte is likely to be higher. FIG. 5B illustrates the output intensity vs. position readout of scanned test strips as provided by a reader device.

Figure 6A:
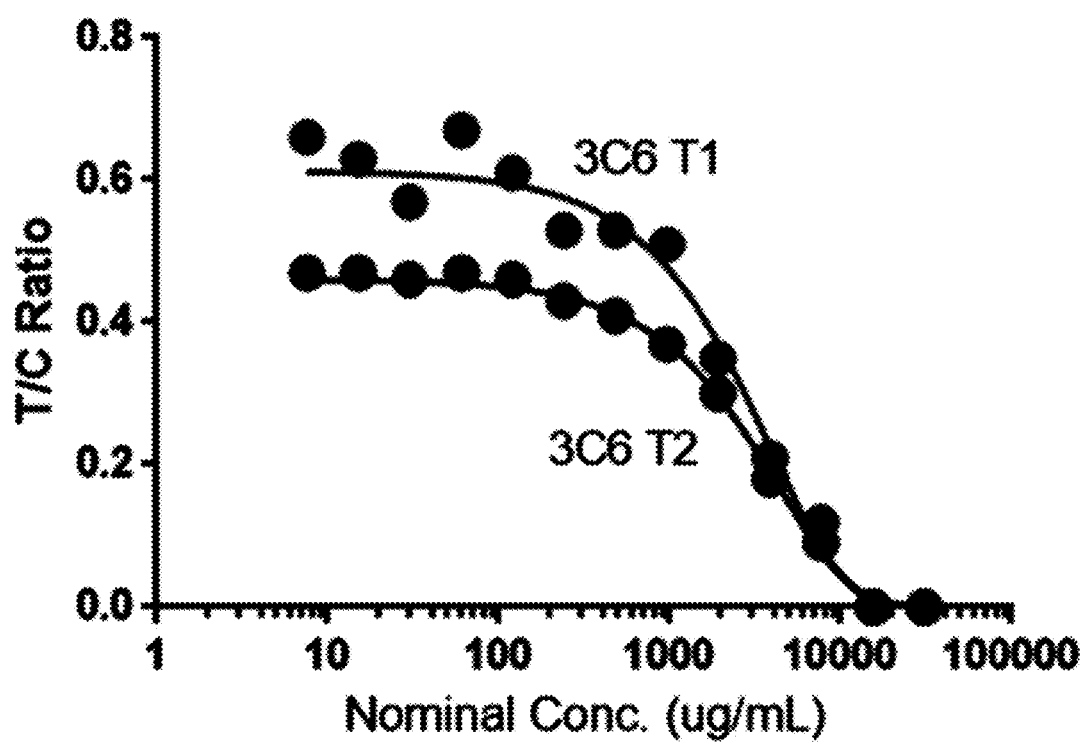
FIGS. 6A and 6B illustrate curves for 3C6 bound at lines T1 and T2 in a representative lateral flow assay of the invention carried out using a device as schematically illustrated in FIG. 2C and as described in Example 3.
Figure 6B:
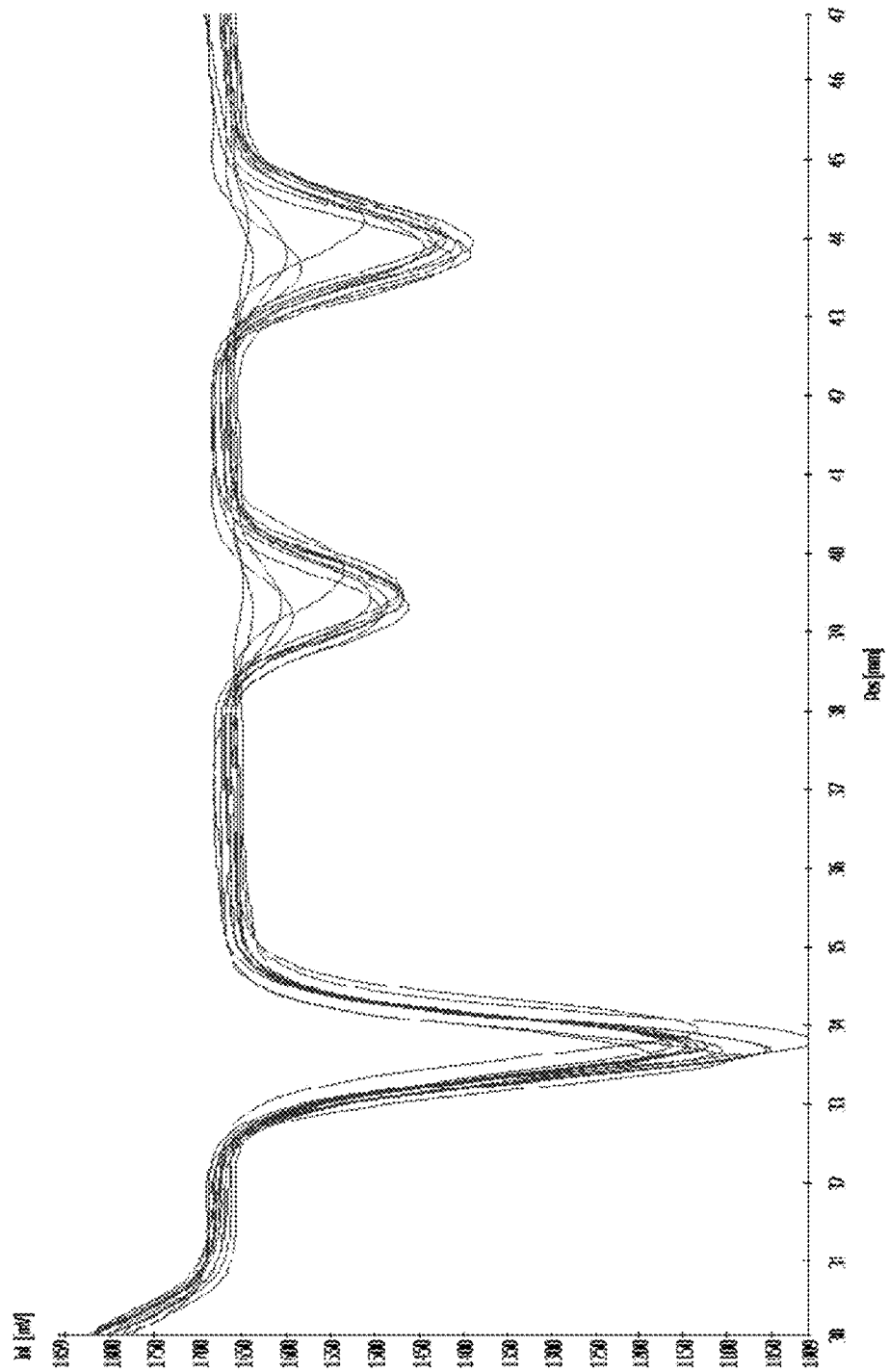

FIGS. 6A and 6B illustrate curves for 3C6 bound at lines T1 and T2. FIG. 6A illustrates the standard curve, i.e., the ratio of test line over control line (T/C) vs. paclitaxel concentration. The relatively minor difference in ratio for 3C6 at T1 versus T2 for the lower concentrations indicates a relatively low improvement in sensitivity would be gained for placing the antibody closer to the sample port, where concentration of analyte is likely to be higher. However, improvement in signal intensity relative to at T2 was observed. FIG. 6B illustrates the output intensity vs. position readout of scanned test strips as provided by a reader device.

Figure 7A:
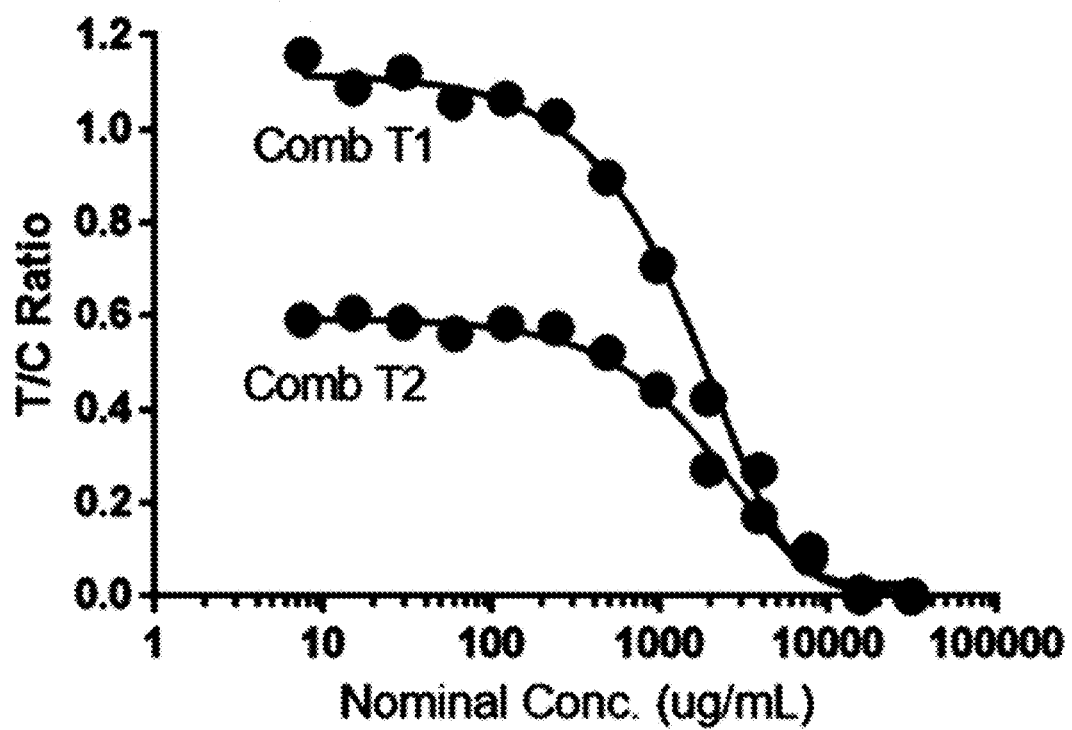
FIGS. 7A and 7B illustrate curves for combined 8A10 and 3C6 bound at lines T1 and T2 in a representative lateral flow assay of the invention carried out using a device as schematically illustrated in FIG. 2C and as described in Example 3.
Figure 7B:
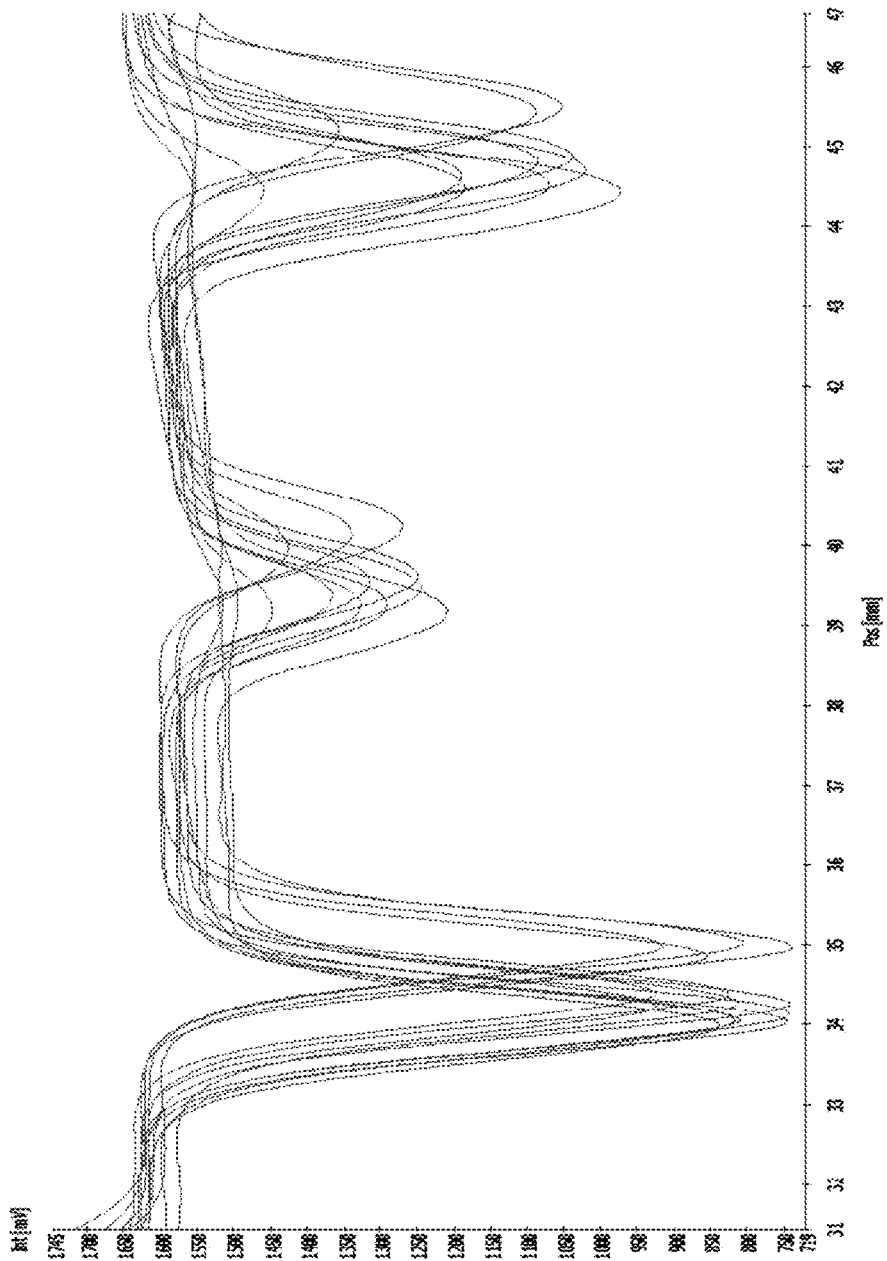

FIGS. 7A and 7B illustrate curves for combined 8A10 and 3C6 bound at lines T1 and T2. FIG. 7A illustrates the standard curve, i.e., the ratio of test line over control line (T/C) vs. paclitaxel concentration. The assay was made more robust by combining the high sensitivity of 8A10 close to the sample port and the higher sensitivity of 3C6 at T2 that is location independent. FIG. 7B illustrates the output intensity vs. position readout of scanned test strips as provided by reader device.

In the above analyses (and in FIGS. 5-7), the measurement of position of T1, T2, and C (Pos [mm]) in FIGS. 5B, 6B, and 7B was made from the downstream end in flow direction (e.g., sample introduced at 55 mm point, T2 at about 45 mm, T1 at about 40 mm, and C at about 35 mm) of the test strip.

EXAMPLE 4

Method for Determining Antibody Binding Properties

In this example, a method for determining antibody properties is described. The methods were carried out by Precision Antibody, Inc. (Columbia, Md.) using a Biacore Assay. This example also shows how the LFA assay of the invention can be adapted to other solid phase assays, such as Surface Plasmon Resonance (SPR) assays.

Binding experiments were performed on a Biacore 3000 instrument (GE, Pittsburgh, Pa.) at 25° C. Approximately 13,000 RU of anti-BSA ab (Life Technologies, A11133, lot 1637270) was directly immobilized on flow cell 2 of CM5 chip by amine coupling (EDC/NHS). 110-120 RU of BSA-paclitaxel (BSA-Ag) was captured. Flow cell 1 was treated the same way but without the ligand and used as a blank surface for reference subtraction. The unoccupied sites were blocked with 1M ethanol amine. Analytes Ab1 (8A10) and Ab2 (3C6) were flowed over the chip at variable concentrations. Binding of antigen to the antibodies was monitored in real time to obtain on ($k_a$) and off ($k_d$) rates. The equilibrium constant ($K_D$) was calculated from the observed $k_a$ and $k_d$.

Full kinetic analysis was performed using analyte concentrations as indicated with 2-fold serial dilutions. The starting concentration was 200 nM, followed by 100, 50, 25, 12.5, and 0 nM. The 100 nM concentration was run in duplicates to confirm the reproducibility of the assay. Full kinetic analysis results are summarized in Table 3.

The assay buffer was 10 mM HEPES buffer (pH 7.4), 150 mM NaCl, 3 mM EDTA, 0.05% P20 (polyoxyethylenesorbitan). The regeneration buffer was 10 mM Glycine buffer (pH 2.0). The conjugation buffer was 10 mM sodium acetate buffer (pH 5.0). The flow rate used for capturing the ligand was 1 μL/min. The flow rate for kinetics analysis was 50 μL/min.

Chi square ($\chi^2$) analysis was carried out between the actual sensorgram and the sensorgram generated from the BIAnalysis software to determine the accuracy of the analysis. A $\chi^2$ value within 1-2 is considered significant (accurate) and below 1 is highly significant (highly accurate).

A summary of three independent SPR runs are presented in Table 4.

TABLE 3

| Full Kinetic Analysis. | | | | | | | | |
|---|---|---|---|---|---|---|---|---|
| Ligand | Analyte | $k_a$ (1/Ms) | $K_d$ (1/s) | $R_{max}$ | $K_A$ (1/M) | $K_D$ (M) | Con (nM) | $\chi^2$ |
| BSA-Ag (110RU) | Ab1 | $4.70 \times 10^5$ | $3.04 \times 10^{-4}$ | 4.01 | $1.55 \times 10^9$ | $6.45 \times 10^{-10}$ | 0-100 | 0.173 |

TABLE 3-continued

Full Kinetic Analysis.

| Ligand | Analyte | $k_a$ (1/Ms) | $K_d$ (1/s) | $R_{max}$ | $K_A$ (1/M) | $K_D$ (M) | Con (nM) | $\chi^2$ |
|---|---|---|---|---|---|---|---|---|
| BSA-Ag (110RU) | Ab2 | $2.05 \times 10^4$ | $9.67 \times 10^{-4}$ | 15.6 | $2.12 \times 10^7$ | $4.72 \times 10^{-8}$ | 0-200 | 0.179 |

TABLE 4

SPR Summary.

| Antibody | Instrument | On the Chip | On-rate | Off-rate | $K_d$ | $R_{max}$ | Note |
|---|---|---|---|---|---|---|---|
| 8A10 | Biacore 3000 | Antibody | $1.6 \times 10^6$ | $2.0 \times 10^{-3}$ | $1.3 \times 10^{-9}$ | 3.6 | |
| | Biacore T-200 | Antibody | $2.4 \times 10^5$ | $8.7 \times 10^{-4}$ | $3.6 \times 10^{-9}$ | 8.6 | |
| | Biacore 3000 | Antigen | $4.7 \times 10^5$ | $3.0 \times 10^{-4}$ | $6.5 \times 10^{-10}$ | 4.0 | |
| 3C6 | Biacore 3000 | Antibody | $2.8 \times 10^4$ | $2.9 \times 10^{-4}$ | $1.0 \times 10^{-8}$ | 54.4 | Single point |
| | Biacore T-200 | Antibody | $1.8 \times 10^4$ | $2.2 \times 10^{-4}$ | $1.2 \times 10^{-8}$ | 112 | |
| | Biacore 3000 | Antigen | $2.1 \times 10^4$ | $9.7 \times 10^{-4}$ | $4.7 \times 10^{-8}$ | 15.6 | |

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for assaying paclitaxel in a liquid sample, comprising:
   (a) applying the liquid sample comprising paclitaxel to a lateral flow assay device, the device comprising
      (i) a sample receiving zone for receiving the liquid sample;
      (ii) a detection reagent zone in liquid communication with the sample receiving zone and downstream in flow direction from the sample receiving zone, wherein the detection reagent zone comprises a detection reagent deposited thereon,
         wherein the detection reagent is a paclitaxel antibody, functional fragment, or functional derivative thereof that binds paclitaxel, wherein the paclitaxel antibody, functional fragment, or functional derivative thereof is labeled with a detectable reporting group,
         wherein the paclitaxel antibody, functional fragment, or functional derivative thereof is selected from
         a first antibody, functional fragment, or functional derivative thereof having a variable light chain amino acid sequence comprising complementarity-determining sequences SEQ ID NO: 9, SEQ ID NO: 10, and SEQ ID NO: 11, and a variable heavy chain amino acid sequence comprising complementarity-determining sequences SEQ ID NO: 12, SEQ ID NO: 13, and GV, or
         a second antibody, functional fragment, or functional derivative thereof having a variable light chain amino acid sequence comprising complementarity-determining sequences SEQ ID NO: 14, SEQ ID NO: 15, and SEQ ID NO: 16, and a variable heavy chain amino acid sequence comprising complementarity-determining sequences SEQ ID NO: 17, SEQ ID NO: 18, and SEQ ID NO: 19; and (iii) a capture zone in liquid communication with the detection reagent zone and downstream in flow direction from the detection reagent zone,
wherein the capture zone comprises first, second, and third capture reagents immobilized thereon,
wherein the first capture reagent is a paclitaxel material capable of binding the detection reagent,
wherein the second capture reagent is a paclitaxel material capable of binding the detection reagent,
wherein the third capture reagent is an antibody capable of binding the detection reagent,
wherein the first capture reagent is positioned at a first distance downstream in flow direction from the upstream end of the capture zone,
wherein the second capture reagent is positioned at a second distance downstream in flow direction from the upstream end of the capture zone,
wherein the third capture reagent is positioned at a third distance downstream in flow direction from the upstream end of the capture zone,
wherein the second distance is greater than the first distance,
wherein the third distance is greater than the first and second distances, and
wherein the ratio of the first distance to the second distance is from greater than about 0.0 to about 0.4, when the paclitaxel antibody, functional fragment, or functional derivative thereof is the first antibody, functional fragment, or functional derivative thereof or
wherein the ratio of the first distance to the second distance is from about 0.2 to about 1.0, when the paclitaxel antibody, functional fragment, or functional derivative thereof is the second antibody, functional fragment, or functional derivative thereof; and (b) allowing the sample to flow from the sample receiving zone through the detection reagent zone to provide detection reagent with paclitaxel;

(c) allowing the detection reagent with paclitaxel to flow through the capture zone,
whereby the first and second capture reagents compete with paclitaxel for binding with the detection reagent, and
whereby the third capture reagent binds excess detection reagent; and (d) observing the amount of detection reagent bound to the first and second capture reagents relative to the third capture reagent.

2. The method of claim 1, wherein the detectable reporting group is colloidal gold.

3. The method of claim 1, wherein the paclitaxel antibody is 3C6.

4. The method of claim 1, wherein the paclitaxel antibody is 8A10.

5. The method of claim 1, wherein the paclitaxel material is a paclitaxel antigen that competes with paclitaxel for binding to the detection reagent.

6. The method of claim 1, wherein the paclitaxel material is a paclitaxel protein conjugate.

7. The method of claim 1 further comprising observing the amount of excess detection reagent bound to the third capture reagent.

8. The method of claim 1 further comprising determining the quantity of paclitaxel in the sample by quantitating the amount of excess detection reagent bound to the third capture reagent.

9. The method of claim 1, wherein the first paclitaxel antibody, functional fragment, or functional derivative thereof,
has a variable light chain amino acid sequence comprising SEQ ID NO: 2 and has a variable heavy chain amino acid sequence comprising SEQ ID NO: 4.

10. The method of claim 1, wherein the second paclitaxel antibody, functional fragment, or functional derivative thereof,
has a variable light chain amino acid sequence comprising SEQ ID NO: 6 and has a variable heavy chain amino acid sequence comprising SEQ ID NO: 8.

11. The method of claim 1 further comprising determining the quantity of paclitaxel in the sample by quantitating the amount of detection reagent bound by the third capture reagent and the first and second capture reagents.

12. The method of claim 11, wherein quantitating the amount of detection reagent bound to the capture reagents comprises optical density measurement.

13. A method for monitoring the efficacy of a paclitaxel therapy in a patient diagnosed with cancer, comprising: (a) treating a cancer patient with paclitaxel at a first point in time; (b) determining a first concentration of paclitaxel in the patient after administering paclitaxel at a first point in time, wherein determining the concentration comprises the method of claim 11; (c) treating the patient with paclitaxel at a second point in time; (d) determining a second concentration of paclitaxel drug in the patient after administering paclitaxel at a second point in time, wherein determining the concentration comprises the methods of claim 11; and (e) comparing the first and second concentrations of paclitaxel in the patient to determine the efficacy of the cancer treatment.

14. A method for pharmacokinetic-guided dosing of paclitaxel therapy in a patient diagnosed with cancer, comprising: (a) treating the cancer patient with paclitaxel at a first point in time; (b) determining one or more pharmacokinetic (PK) parameters of paclitaxel in the patient after administering paclitaxel at a first point in time, wherein determining the one or more pharmacokinetic parameters comprises measuring the concentration of paclitaxel by method of claim 11; (c) treating the patient with paclitaxel at a second point in time using the PK parameters from the first dosing; (d) determining one or more pharmacokinetic parameters of paclitaxel in the patient after administering paclitaxel at a second point in time, wherein determining the one or more pharmacokinetic parameters comprises measuring the concentration of paclitaxel by the method of claim 11; and (e) comparing one or more pharmacokinetic parameters of paclitaxel in the subject at the first point in time with the levels at the second point in time to confirm that optimal dosing was achieved.

15. The method of claim 14, wherein the pharmacokinetic parameters are selected from the group consisting of time to maximum concentration ($T_{max}$), concentration maximum ($C_{max}$), area under the curve (AUC), clearance (CL), volume of distribution ($V_d$), apparent volume of distribution during the terminal phase (Vz), apparent volume of distribution during steady state ($V_{ss}$) and combinations thereof.

* * * * *

SEQUENCE LISTING

<160> NUMBER OF SEQ ID NOS: 19

<210> SEQ ID NO 1
<211> LENGTH: 323
<212> TYPE: DNA
<213> ORGANISM: Artificial Sequence
<220> FEATURE:
<223> OTHER INFORMATION: Synthetic

<400> SEQUENCE: 1
gacattgtga tgacccagtc tcaaaaattc atgtccataa cactaggaga gagggtcagc      60
atcacctgca agcccagtca gaatgtgggt tctgctgtaa cctggtggca acagaaacca     120
ggacaatctc ctaaactact gatttactca gcttccaatc ggtatactgg agtccctgat     180
cgcttcacag gcagtggatc tgggacagat ttcactctca ccattagtaa tgtgcagtct     240
gaagacctgg cagattattt ctgtcaacaa tatagcagct atccgtacac gttcggaggg     300
gggaccaagc tggaaataaa acg                                             323

<210> SEQ ID NO 2
<211> LENGTH: 108
<212> TYPE: PRT
<213> ORGANISM: Artificial Sequence
<220> FEATURE:
<223> OTHER INFORMATION: Synthetic

<400> SEQUENCE: 2

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Asn Val Gly Ser Ala
            20                  25                  30

Val Thr Trp Trp Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

```
Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Tyr
                 85                  90                  95

Thr Phe Gly Gly Gly Thr Lys Leu Glu Ile Lys Arg
            100                 105
```

<210> SEQ ID NO 3
<211> LENGTH: 333
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(333)

<400> SEQUENCE: 3

```
gag gtc cag ctg caa caa tct gga cct gaa ctg gtg aag cct ggg gct       48
Glu Val Gln Leu Gln Gln Ser Gly Pro Glu Leu Val Lys Pro Gly Ala
 1               5                  10                  15 tca gtg aag att tcc tgt aag gct tct gga tac acg ttc act gac tcc       96
Ser Val Lys Ile Ser Cys Lys Ala Ser Gly Tyr Thr Phe Thr Asp Ser
             20                  25                  30 acc atg aac tgg gtg aag cag agc cat gga aag agc ctt gag tgg att      144
Thr Met Asn Trp Val Lys Gln Ser His Gly Lys Ser Leu Glu Trp Ile
         35                  40                  45 gga gag att gat cct aac aat ggt ggt act aac tac aat cag aag ttc      192
Gly Glu Ile Asp Pro Asn Asn Gly Gly Thr Asn Tyr Asn Gln Lys Phe
     50                  55                  60 aag ggc aag gcc aca ttg act gta gac aag tcc tcc agc aca gcc tat      240
Lys Gly Lys Ala Thr Leu Thr Val Asp Lys Ser Ser Ser Thr Ala Tyr
 65                  70                  75                  80 atg gag ctc cgc agc ctg aca tct gag gac tct gca gtc tat tac tgt      288
Met Glu Leu Arg Ser Leu Thr Ser Glu Asp Ser Ala Val Tyr Tyr Cys
                 85                  90                  95 gca aga ggg gtc tgg ggc caa ggc acc act ctc aca gtc tcc tca          333
Ala Arg Gly Val Trp Gly Gln Gly Thr Thr Leu Thr Val Ser Ser
            100                 105                 110
```

<210> SEQ ID NO 4
<211> LENGTH: 111
<212> TYPE: PRT
<213> ORGANISM: Artificial Sequence
<220> FEATURE:
<223> OTHER INFORMATION: Synthetic Construct

<400> SEQUENCE: 4

```
Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Ser
             20                  25                  30

Thr Met Asn Trp Val Lys Gln Ser His Gly Lys Ser Leu Glu Trp Ile
         35                  40                  45

Gly Glu Ile Asp Pro Asn Asn Gly Gly Thr Asn Tyr Asn Gln Lys Phe
     50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95
```

Ala Arg Gly Val Trp Gly Gln Gly Thr Thr Leu Thr Val Ser Ser
            100                 105                 110

<210> SEQ ID NO 5
<211> LENGTH: 337
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(336)

<400> SEQUENCE: 5

```
gat gtt gtg atg acc caa act cca ctc tcc ctg cct gtc agt ctg gga      48
Asp Val Val Met Thr Gln Thr Pro Leu Ser Leu Pro Val Ser Leu Gly
1               5                   10                  15 gat caa gcc tcc atc tct tgc aga tct cgt cag agc ctt gta cac agt      96
Asp Gln Ala Ser Ile Ser Cys Arg Ser Arg Gln Ser Leu Val His Ser
            20                  25                  30 aat gga aac acc tat tta cat tgg tac ctg cag aag cca ggc cag tct    144
Asn Gly Asn Thr Tyr Leu His Trp Tyr Leu Gln Lys Pro Gly Gln Ser
        35                  40                  45 cca aag ctc ctg atc tac aaa gtt tcc aac cga ttt tct ggg gtc cca    192
Pro Lys Leu Leu Ile Tyr Lys Val Ser Asn Arg Phe Ser Gly Val Pro
    50                  55                  60 gac agg ttc agt ggt agt gga tca ggg aca gaa ttc aca ctc gag atc    240
Asp Arg Phe Ser Gly Ser Gly Ser Gly Thr Glu Phe Thr Leu Glu Ile
65                  70                  75                  80 agc aga gtg gag gct gag gat ctg gga gtt tat ttc tgc tct caa agt    288
Ser Arg Val Glu Ala Glu Asp Leu Gly Val Tyr Phe Cys Ser Gln Ser
                85                  90                  95 aca cat gtt cct ccg acg ttc ggt gga ggc acc aag ctg gaa atc aaa c  337
Thr His Val Pro Pro Thr Phe Gly Gly Gly Thr Lys Leu Glu Ile Lys
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: Synthetic Construct

<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 7
<211> LENGTH: 339
<212> TYPE: DNA

<213> ORGANISM: Artificial Sequence
<220> FEATURE:
<223> OTHER INFORMATION: Synthetic
<220> FEATURE:
<221> NAME/KEY: CDS
<222> LOCATION: (1)..(339)

<400> SEQUENCE: 7

```
gag gtg cag ctt cag gag tcg gga cct agt ctc gtg aaa cct tct cag      48
Glu Val Gln Leu Gln Glu Ser Gly Pro Ser Leu Val Lys Pro Ser Gln
1               5                   10                  15 act ctg tcc ctc acc tgt tct gtc act ggc gac tcc atc acc agt ggt      96
Thr Leu Ser Leu Thr Cys Ser Val Thr Gly Asp Ser Ile Thr Ser Gly
            20                  25                  30 tac tgg aac tgg atc cgg aaa ttc cca ggg aat aga ctt gag tac atg     144
Tyr Trp Asn Trp Ile Arg Lys Phe Pro Gly Asn Arg Leu Glu Tyr Met
        35                  40                  45 ggg tac ata agc tac agt ggt agc act tac tac aat ccg tct ctc aaa     192
Gly Tyr Ile Ser Tyr Ser Gly Ser Thr Tyr Tyr Asn Pro Ser Leu Lys
    50                  55                  60 agt cga atc tcc atc act cga gac aca tcc aag aac cag tac tac cta     240
Ser Arg Ile Ser Ile Thr Arg Asp Thr Ser Lys Asn Gln Tyr Tyr Leu
65                  70                  75                  80 cat ttg act tct gtg act act gag gac aca gcc aca tat tac tgt gcc     288
His Leu Thr Ser Val Thr Thr Glu Asp Thr Ala Thr Tyr Tyr Cys Ala
                85                  90                  95 caa ggg gat ggc gcc tac tgg ggc caa ggc acc act ctc aca gtc tcc     336
Gln Gly Asp Gly Ala Tyr Trp Gly Gln Gly Thr Thr Leu Thr Val Ser
            100                 105                 110 tca                                                                  339
Ser
```

<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Arg Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

His Leu Thr Ser Val Thr Thr Glu Asp Thr Ala Thr Tyr Tyr Cys Ala
                85                  90                  95

Gln Gly Asp Gly Ala Tyr Trp Gly Gln Gly Thr Thr Leu Thr Val Ser
            100                 105                 110

Ser
```

<210> SEQ ID NO 9
<211> LENGTH: 11
<212> TYPE: PRT
<213> ORGANISM: Artificial Sequence
<220> FEATURE:

```
<223> OTHER INFORMATION: Synthetic

<400> SEQUENCE: 9

Lys Pro Ser Gln Asn Val Gly Ser Ala Val Thr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Ser Ala Ser Asn Arg Tyr Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Gln Gln Tyr Ser Ser Tyr Pro Tyr Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Gly Tyr Thr Phe Thr Asp Ser Thr Met Asn
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Glu Ile Asp Pro Asn Asn Gly Gly Thr Asn Tyr Asn Gln Lys Phe Lys
1               5                   10                  15

Gly

<210> SEQ ID NO 14
<211> LENGTH: 16
<212> TYPE: PRT
<213> ORGANISM: Artificial Sequence
<220> FEATURE:
<223> OTHER INFORMATION: Synthetic

<400> SEQUENCE: 14

Arg Ser Arg Gln Ser Leu Val His Ser Asn Gly Asn Thr Tyr Leu His
1               5                   10                  15

<210> SEQ ID NO 15
<211> LENGTH: 7
<212> TYPE: PRT
<213> ORGANISM: Artificial Sequence
```

<220> FEATURE:
<223> OTHER INFORMATION: Synthetic

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ser Gln Ser Thr His Val Pro Pro Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gly Asp Ser Ile Thr Ser Gly Tyr Trp Asn
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic

<400> SEQUENCE: 18

Tyr Ile Ser Tyr Ser Gly Ser Thr Tyr Tyr Asn Pro Ser Leu Lys Ser
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Gly Asp Gly Ala Tyr
1               5